(12) United States Patent
Gelfand et al.

(10) Patent No.: US 7,141,377 B2
(45) Date of Patent: *Nov. 28, 2006

(54) PROCESS FOR DISCRIMINATION OF NUCLEIC ACID SEQUENCE VARIANTS

(75) Inventors: David H. Gelfand, Oakland, CA (US); Pamela M. Holland, Seattle, WA (US); Randall K. Saiki, Richmond, CA (US); Robert M. Watson, Berkeley, CA (US)

(73) Assignee: Roche Molecular Systems, Inc., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/043,099

(22) Filed: Jan. 27, 2005

(65) Prior Publication Data

US 2005/0255499 A1    Nov. 17, 2005

Related U.S. Application Data

(63) Continuation of application No. 09/570,179, filed on May 12, 2000, now abandoned, which is a continuation of application No. 08/934,378, filed on Sep. 19, 1997, now Pat. No. 6,214,979, which is a continuation of application No. 08/428,941, filed on Apr. 25, 1995, now Pat. No. 5,804,375, which is a continuation of application No. 07/961,884, filed as application No. PCT/US91/05571 on Aug. 6, 1991, now Pat. No. 5,487,972, which is a continuation-in-part of application No. 07/563,758, filed on Aug. 6, 1990, now Pat. No. 5,210,015.

(51) Int. Cl.
*C12Q 1/68*    (2006.01)
*C12P 19/34*   (2006.01)

(52) U.S. Cl. .................. 435/6; 435/91.1; 435/91.2; 435/810; 436/501; 536/23.1; 536/24.1; 536/24.3; 536/24.31; 536/24.32; 536/24.33; 935/77; 935/78; 935/88

(58) Field of Classification Search ............ None
See application file for complete search history.

(56) References Cited

U.S. PATENT DOCUMENTS

| | | | |
|---|---|---|---|
| 4,318,981 A | 3/1982 | Burd et al. ................ 435/7 |
| 4,656,127 A | 4/1987 | Mundy ...................... 435/6 |
| 4,683,194 A | 7/1987 | Saiki et al. ................ 435/6 |
| 4,683,195 A | 7/1987 | Mullis et al. .............. 435/6 |
| 4,683,202 A | 7/1987 | Mullis ..................... 435/91 |
| 4,743,535 A | 5/1988 | Carrico .................... 435/6 |
| 4,780,405 A | 10/1988 | Kaiser et al. ............. 435/6 |
| 4,851,331 A | 7/1989 | Vary et al. | |
| 4,876,335 A | 10/1989 | Yamane et al. ........... 536/27 |
| 4,889,818 A | 12/1989 | Gelfand et al. .......... 435/194 |
| 4,914,210 A | 4/1990 | Levenson et al. ........ 548/413 |
| 5,011,769 A | 4/1991 | Duck et al. ............... 435/6 |
| 5,108,892 A | 4/1992 | Burke et al. ............. 435/6 |
| 5,210,015 A | 5/1993 | Gelfand et al. ........... 435/6 |
| 5,487,972 A | 1/1996 | Gelfand et al. ........... 435/6 |
| 5,804,375 A * | 9/1998 | Gelfand et al. ........... 435/6 |
| 6,214,979 B1 | 4/2001 | Gelfand et al. ......... 536/22.1 |

FOREIGN PATENT DOCUMENTS

| | | |
|---|---|---|
| EP | 0 063 879 A2 | 11/1982 |
| EP | 70685 A2 * | 1/1983 |
| EP | 0 117 777 A1 | 9/1984 |
| EP | 0 200 362 A2 | 12/1986 |
| EP | 0 201 184 A2 | 12/1986 |
| EP | 0 214 908 A1 | 3/1987 |
| EP | 0 229 943 A2 | 7/1987 |
| EP | 0 232 967 A2 | 8/1987 |
| EP | 0 237 362 A1 | 9/1987 |
| EP | 0 251 283 A2 | 1/1988 |
| EP | 0 258 017 A2 | 3/1988 |
| EP | 0 210 184 B1 | 4/1988 |
| EP | 0 320 308 A2 | 6/1989 |
| EP | 0 330 221 A2 | 8/1989 |
| EP | 0 334 694 A1 | 9/1989 |
| EP | 0 063 879 B1 | 11/1989 |
| EP | 0 357 011 | 3/1990 |
| EP | 0 229 943 B1 | 9/1991 |
| EP | 0 237 362 B1 | 3/1992 |
| EP | 0 200 362 B1 | 1/1993 |
| WO | WO 89/09284 | 10/1989 |
| WO | WO 89/10979 | 11/1989 |
| WO | WO 89/11548 | 11/1989 |
| WO | WO 90/12115 | 10/1990 |

OTHER PUBLICATIONS

Morrison et al. ("Solution-phase detection of polynucleotides using interacting fluorescent labels and competitive hybridization" Anal Biochem. Dec. 1989; 183(2):231-4.*

Abe et al., "Ribonuclease A Cleavage Combined with the Polymerase Chain Reaction for Detection of the Z Mutation of the Alpha-1-antitrypsin Gene," *American J. of Respiratory Cell and Molecular Biology* 1: 331-334.

BioLabs, "Enzymes for Custom Digest," http://www.neb.com/nebecomm/default.asp, Jun. 9, 2005.

Brumbaugh, J.A., Middendorf, L.R., Grone, D.L., and Ruth, J.L., (1988) "Continuous, On-line DNA Sequencing Using Oligodeoxynucleotide Primers with Multiple Fluorophores," *Proc. Natl. Acad. Sci. USA* 85: 5610-5614.

Cardullo, R.A., Agrawal, S., Flores, C., Zamecnik, P.C. and Wolf, D.E., (1988) "Detection of nucleic acids by nonradiative fluorescence resonance energy transfer," *Proc. Natl. Acad. Sci. USA* 85: 8790-8794.

(Continued)

Primary Examiner—Kenneth R. Horlick
Assistant Examiner—Christopher M. Babic
(74) Attorney, Agent, or Firm—Charles M. Doyle

(57) ABSTRACT

A process of detecting a target nucleic acid using labeled oligonucleotides uses the 5' to 3' nuclease activity of a nucleic acid polymerase to cleave annealed labeled oligonucleotide from hybridized duplexes and release labeled oligonucleotide fragments for detection. This process is easily incorporated into a PCR amplification assay.

21 Claims, 18 Drawing Sheets

OTHER PUBLICATIONS

Gelfand, David H., "Taq DNA Polymerase" in PCR Technology, Erlich, ed., Stockton Press, 1989, pp. 17-22.

European Search Report Dec. 3, 2003, European Patent Office.

Haralambidis, J., Duncan, L., Angus, K., and Treger G.W., (1990) "The Synthesis of Polyamide—Oligonucleotide Conjugate Molecules," *Nucleic Acids Res.* 18: 493-499.

Heller, Michael J. and Morrison, Larry E., "Chemiluminescent and Fluorescent Probes for DNA Hybridization Systems," in Rapid Detection and Identification of Infectious Agents, Academic Press, Inc., 1985, pp. 245-256.

Lawyer et al., "Isolation, Characterization, and Expression in *Escherichia coli* of the DNA Polymerase Gene from Thermus Aquatics," *J. Biol. Chem.* 264(11):6427-6437.

Lehman et al., "Persistence of Deoxyribonucleic Acid Polymerase I and Its 5'—3'Exonuclease Activity in PolA Mutants of *Escherichia coli* K12," *J. Biol. Chem.* 248(22):7717-7723.

Minta, A., Kao, J.P. & Tsien, R.Y. (1989) "Fluorescent indicators for cytosolic calcium based on rhodamine and fluorescein chromophores," *J. Biol. Chem.* 264, 8171-8178.

Molecular Cloning, Cold Spring Harbor Laboratory, Cold Spring Harbor, New York, pp. 108-109 (1989).

Morrison, L.E., Hadler, T.C. and Stols, L.M. (1989) "Solution phase detection of polynucleotides using interacting fluorescent labels and competitive hybridization," *Anal. Biochem.* 183: 231-244.

Nelson, P. S., Frye, R. A., and Liu, E., (1989) "Bifunctional Oligonucleotide Probes are Able to Detect Single Base Pair Mutations," *Nucleic Acids Res.* 17, 7187-7194.

Rossiter et al., "Molecular Scanning Methods of Mutation Detection," *The Journal of Biological Chemistry* 265: 12753-12756.

Setlow et al., "Deoxyribonucleic Acid Polymerase: Two Distinct Enzymes in One Polypeptide," *J. Biology Chemistry*, 247(1):224-231.

Smith, L.M., Fung, S., Hunkapiller, M. W., Hunkapiller, T.J., and Hood, L.E., (1985) "The Synthesis of Oligonucleotides Containing an Allphatic Amino Group at the 5'Terminus," *Nucleic Acids Res.* 13: 2399-2412.

Thuong, N. T., (1987) "Synthese et Reactivite D'Oligothymidylates Substitutes Par un Agent Intercalant et un Groupe Thiophosphate," *Tetrahedron Letters* 28: 4157-4160.

Tournon, Jacques, (1975) "Fluorescent Probing of Nucleic Acids: I. Singly and Doubly Labeled Dithymidine Phosphate: Fluorescence and Energy Transfer Studies," *Nucleic Acids Res.* 2, 1261-1273.

Ullman, E.F., Schwarzberg, M., and Rubenstein, K.E., (1976) "Fluorescent Excitation Transfer Immunoassay," *J. Biol. Chem.* 251: 4172-4178.

* cited by examiner

LANE  1 2 3 4 5 6 7 8 9 10 11 12

LANE  1 2 3 4 5 6 7 8 9 10 11 12

BIOTIN HYDRAZIDE

BIOTIN LONG CHAIN HYDRAZIDE

SEQUENCE LISTING

<160> NUMBER OF SEQ ID NOS: 24

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
ccgatagttt gagttcttct actcaggc                                      28

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
gaagaaagcg aaaggagcgg gcgctagggc                                    30

<210> SEQ ID NO 3
<211> LENGTH: 30
<212> TYPE: DNA
<213> ORGANISM: Artificial Sequence

```
<220> FEATURE:
<223> OTHER INFORMATION: Description of Artificial Sequence:
      Oligonucleotide
<220> FEATURE:
<221> NAME/KEY: misc_feature
<222> LOCATION: (30)
<223> OTHER INFORMATION: 3'-PO4

<400> SEQUENCE: 3
cgctgcgcgt aaccaccaca cccgccgcgc                                          30

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: misc_feature
<222> LOCATION: (36)
<223> OTHER INFORMATION: 3'-PO4

<400> SEQUENCE: 4
gatcgctgcg cgtaaccacc acacccgccg ccgcgc                                   36

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: misc_feature
<222> LOCATION: (40)
<223> OTHER INFORMATION: 3'-PO4

<400> SEQUENCE: 5
cgtcaccgat cgctgcgcgt aaccaccaca cccgccgcgc                               40

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
gatgagttcg tgtccgtaca actgg                                               25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
ggttatcgaa atcagccaca gcgcc                                               25

<210> SEQ ID NO 8
<211> LENGTH: 30
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 8
cgctgcgcgt aaccaccaca cccgccgcgc                              30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gatcgctgcg cgtaaccacc acacccgccg cgc                          33

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
cgtcaccgat cgctgcgcgt aaccaccaca cccgccgcgc                   40

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gcgctagggc gctggcaagt gtagcggtca                              30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
ggcgctaggg cgctggcaag tgtagcggtc                              30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
gggcgctagg gcgctggcaa gtgtagcggt                              30

<210> SEQ ID NO 14
<211> LENGTH: 30
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 14
agcgggcgct agggcgctgg caagtgtagc                                          30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
aaaggagcgg gcgctagggc gctggcaagt                                          30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gaagaaagcg aaaggagcgg gcgctagggc                                          30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
cggccaacgc gcggggagag gcggtttgcg                                          30

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
tatcccgccg cgcttaatgc gccgctaca                                           29

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
gcattaatgc gccgctacag ggcgcgtact atgg                                     34
```

```
<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gagaccatca atgaggaagc tgcagaatgg gat                              33

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gtggagacca tcaatgagga agctgcagaa tgggat                           36

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
agtgggggga catcaagcag ccatgcaaat                                  30

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
tgctatgtca gttccccttg gttctct                                     27

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
gagaccatca atgaggaagc tgcagaatgg gat                              33
```

PROCESS FOR DISCRIMINATION OF NUCLEIC ACID SEQUENCE VARIANTS

RELATED APPLICATIONS

This is a continuation application of U.S. application Ser. No. 09/570,179, filed May 12, 2000, now abandoned which is a continuation of U.S. application Ser. No. 08/934,378, filed Sep. 19, 1997, now U.S. Pat. No. 6,214,979, which is a continuation of U.S. application Ser. No. 08/428,941, filed Apr. 25, 1995, now U.S. Pat. No. 5,804,375, which is a continuation of U.S. application Ser. No. 07/961,884, filed Jan. 5, 1993, now U.S. Pat. No. 5,487,972, which was filed under 35 U.S.C. § 371 as a National Stage of international application No. PCT/US91/05571, filed Aug. 6, 1991, which is a continuation-in-part of U.S. application Ser. No. 07/563,758, filed Aug. 6, 1990, now U.S. Pat. No. 5,210,015, all of which are herein incorporated by reference in their entirety.

This invention relates generally to the field of nucleic acid chemistry. More specifically, it relates to the use of the 5' to 3' nuclease activity of a nucleic acid polymerase to degrade a labeled oligonucleotide in a hybridized duplex composed of the labeled oligonucleotide and a target oligonucleotide sequence and form detectable labeled fragments.

Investigational microbiological techniques are routinely applied to diagnostic assays. For example, U.S. Pat. No. 4,358,535 discloses a method for detecting pathogens by spotting a sample (e.g., blood, cells, saliva, etc.) on a filter (e.g., nitrocellulose), lysing the cells, and fixing the DNA through chemical denaturation and heating. Then, labeled DNA probes are added and allowed to hybridize with the fixed sample DNA, hybridization indicating the presence of the pathogen's DNA. The sample DNA in this case may be amplified by culturing the cells or organisms in place on the filter.

A significant improvement in DNA amplification, the polymerase chain reaction (PCR) technique, is disclosed in U.S. Pat. Nos. 4,683,202; 4,683,195; 4,800,159; and 4,965,188. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing, and the extension of the annealed primers by DNA polymerase results in the exponential accumulation of a specific fragment whose termini are defined by the 5' ends of the primers. PCR is capable of producing a selective enrichment of a specific DNA sequence by a factor of $10^9$. The PCR method is also described in Saiki et al., 1985, *Science* 230:1350.

Detection methods generally employed in standard PCR techniques use a labeled probe with the amplified DNA in a hybridization assay. For example, EP Publication No. 237,362 and PCT Publication No. 89/11548 disclose assay methods wherein the PCR-amplified DNA is first fixed to a filter, and then a specific oligonucleotide probe is added and allowed to hybridize. Preferably, the probe is labeled, e g., with $^{32}$P, biotin, horseradish peroxidase (HRP), etc., to allow for detection of hybridization. The reverse is also suggested, that is, the probe is instead bound to the membrane, and the PCR-amplified sample DNA is added.

Other means of detection include the use of fragment length polymorphism (PCR-FLP), hybridization to allele-specific oligonucleotide (ASO) probes (Saiki et al., 1986, *Nature* 324:163), or direct sequencing via the dideoxy method using amplified DNA rather than cloned DNA. The standard PCR technique operates essentially by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, tetramethylbenzidine (TMB) and hydrogen peroxide are added: HRP catalyzes the hydrogen peroxide oxidation of TMB to a soluble blue dye that can be precipitated, indicating hybridized probe.

While the PCR technique as presently practiced is an extremely powerful method for amplifying nucleic acid sequences, the detection of the amplified material requires additional manipulation and subsequent handling of the PCR products to determine whether the target DNA is present. It would be desirable to decrease the number of subsequent handling steps currently required for the detection of amplified material. A "homogeneous" assay system, that is, one which generates signal while the target sequence is amplified, requiring minimal post-amplification handling, would be ideal.

The present invention provides a process for the detection of a target nucleic acid sequence in a sample, said process comprising:

(a) contacting a sample comprising single-stranded nucleic acids with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3' end of the first oligonucleotide is adjacent to the 5' end of the labeled oligonucleotide;

(b) maintaining the mixture of step (a) with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments; and (c) detecting and/or measuring the release of labeled fragments.

This process is especially suited for analysis of nucleic acid amplified by PCR. This process is an improvement over known PCR detection methods because it allows for both amplification of a target and the release of a label for detection to be accomplished in a reaction system without resort to multiple handling steps of the amplified product. Thus, in another embodiment of the invention, a polymerase chain reaction amplification method for concurrent amplification and detection of a target nucleic acid sequence in a sample is provided. This method comprises:

(a) providing to a PCR assay containing said sample, at least one labeled oligonucleotide containing a sequence complementary to a region of the target nucleic acid, wherein said labeled oligonucleotide anneals within the target nucleic acid sequence bounded by the oligonucleotide primers of step (b);

(b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand;

(c) amplifying the target nucleic acid sequence employing a nucleic acid polymerase having 5' to 3' nuclease activity as a template-dependent polymerizing agent under conditions which are permissive for PCR cycling steps of (i) annealing of primers and labeled oligonucleotide to a template nucleic acid sequence contained within the target region, and (ii) extending the primer, wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and (d) detecting and/or measuring the release of labeled fragments to determine the presence or absence of target sequence in the sample.

Figure 7A:
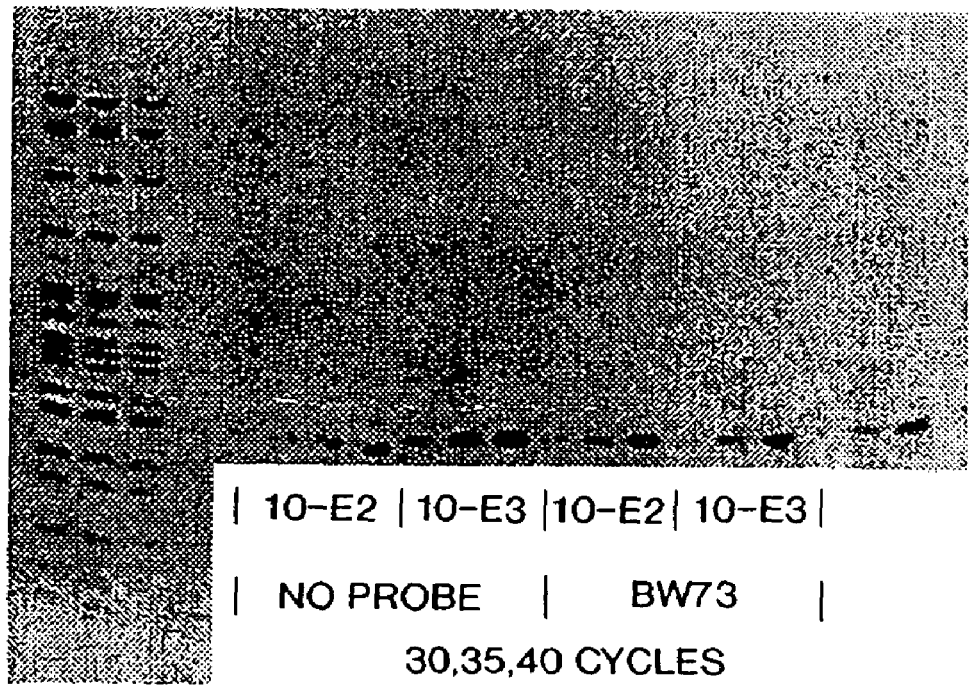
Figure 7B:
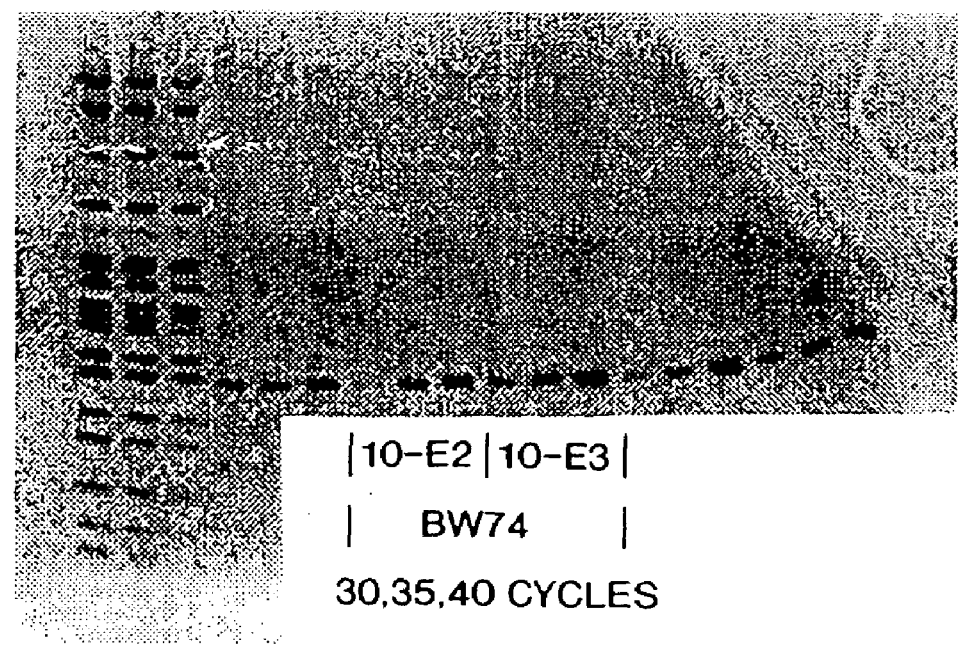

FIG. 7 provides 5% acrylaride electrophoresis gel analysis of a 142 base pair HIV product, amplified in the presence or absence of labeled probe.

Figure 8A:
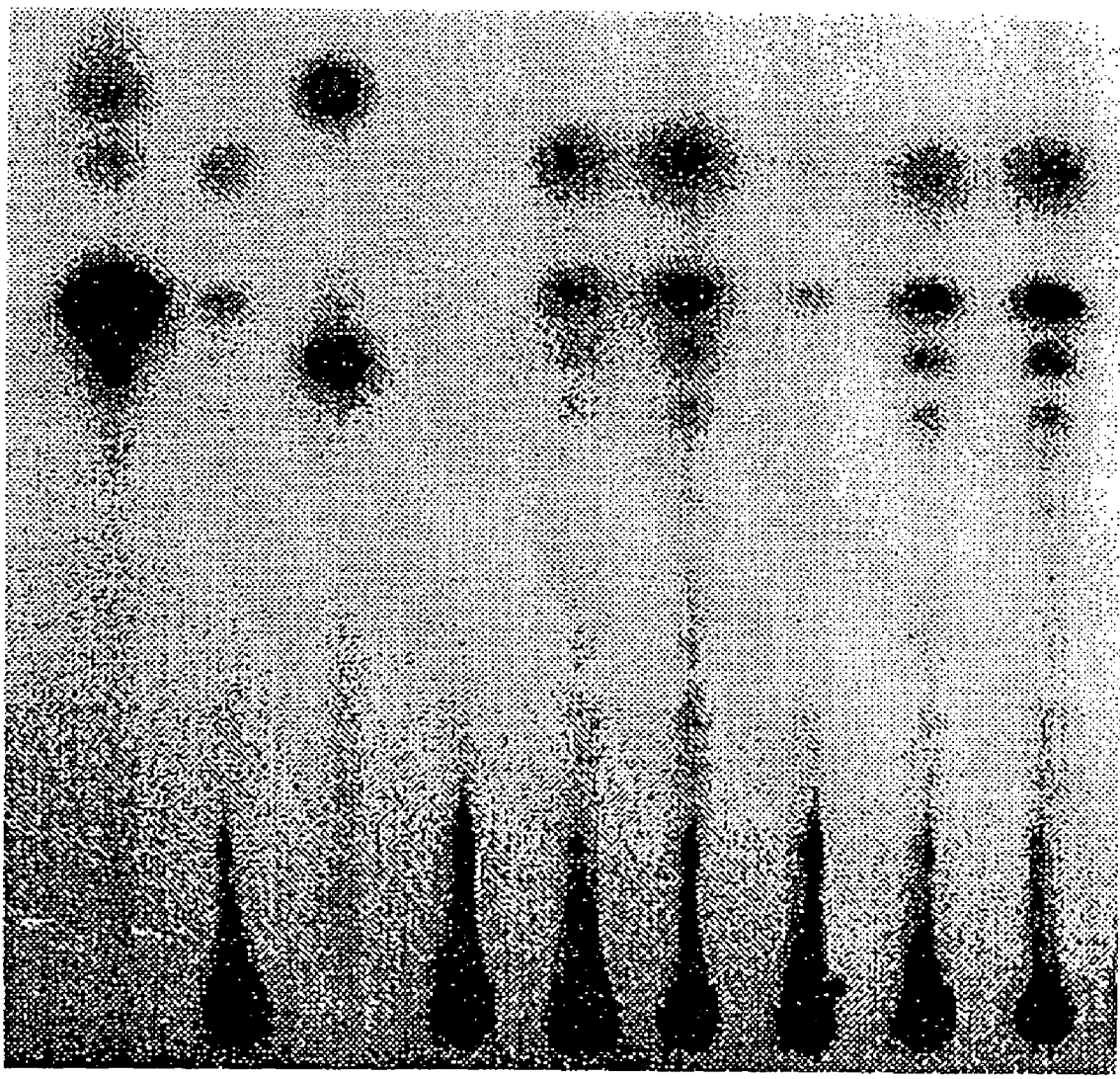
Figure 8B:
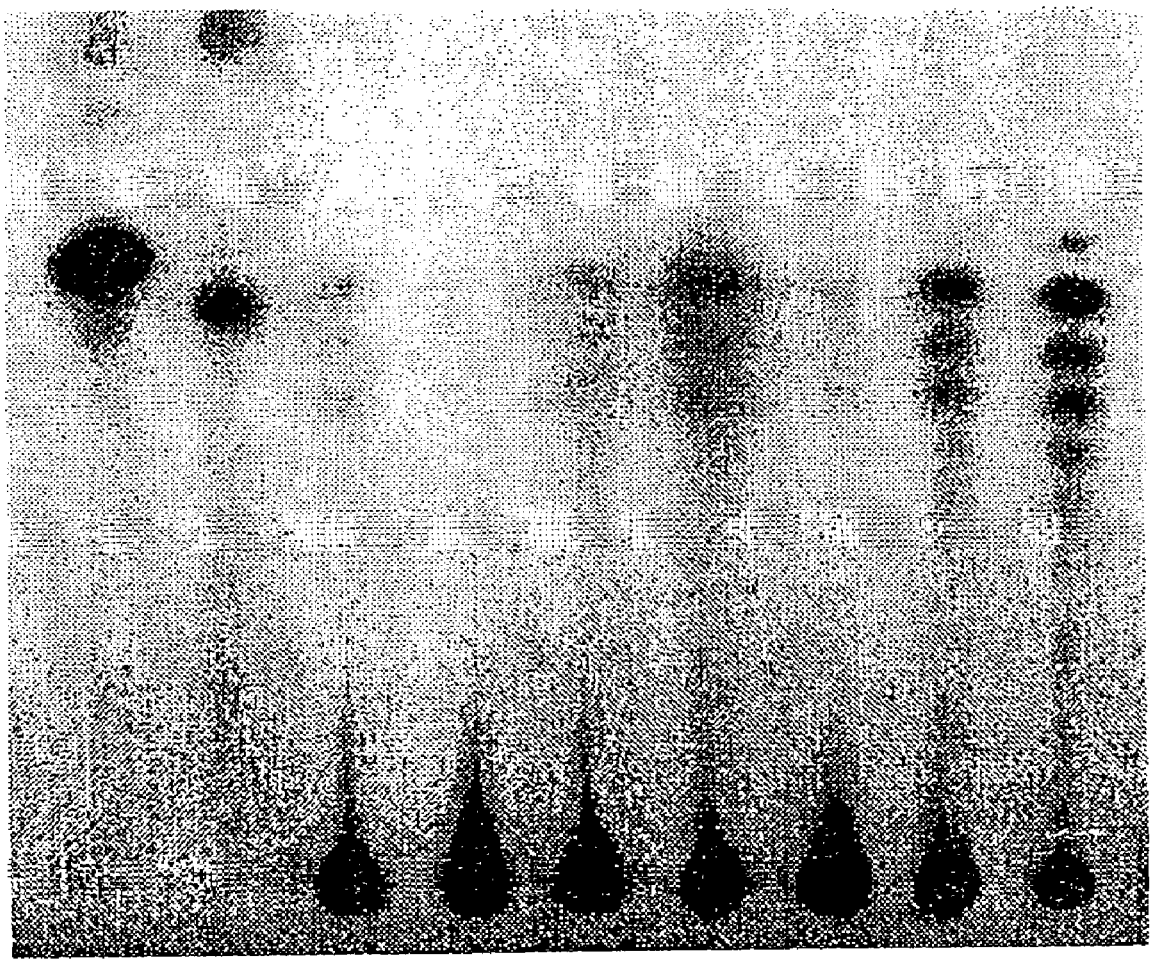

FIG. 8 is a composite of two autoradiographs of TLC analysis of aliquots of PCR amplification products which show that radiolabel release occurs and increases in amount with both increases in starting template and with longer thermocycling.

Figure 9:
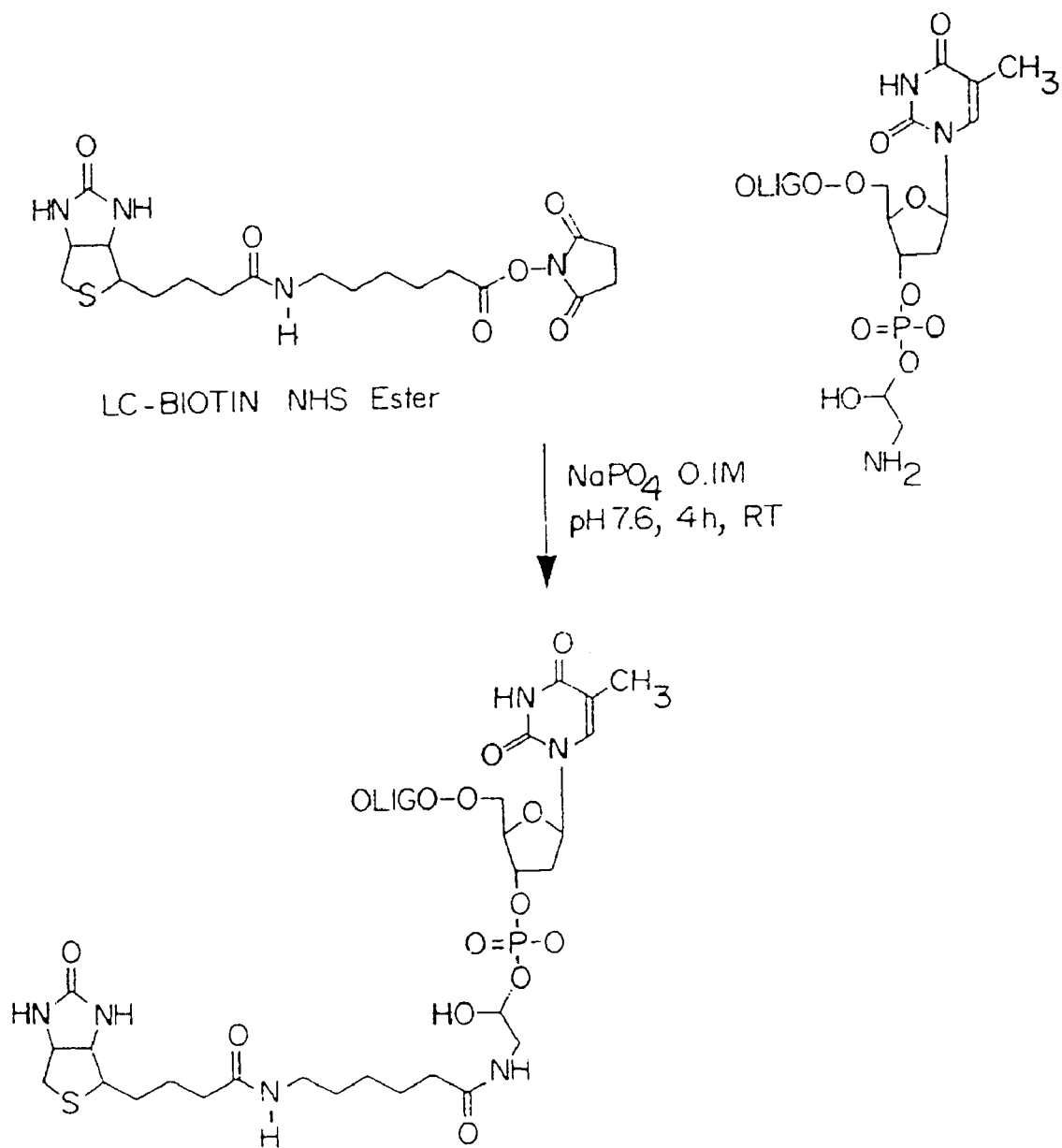

FIG. 9 is a schematic for a reaction in which an NHS-active ester derivative of biotin is added to the 3'-amine of an oligonucleotide probe.

Figure 10:
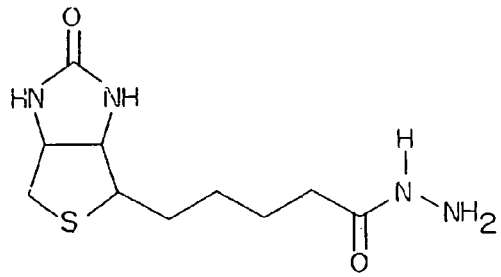
Figure 10:
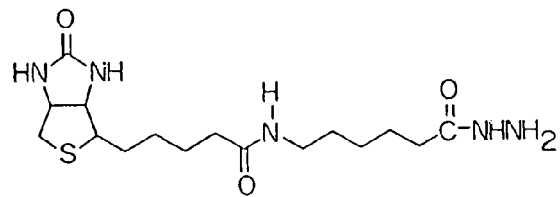
Figure 10:
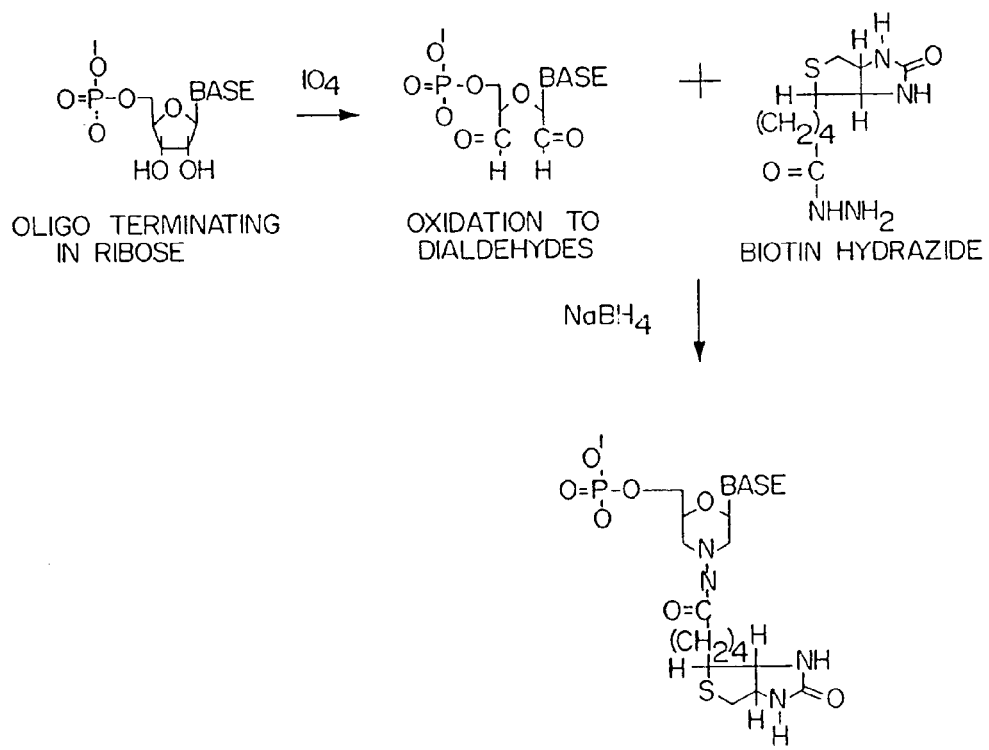

FIG. 10 is a schematic for a reaction in which a biotin hydrazide is used to label an oligonucleotide probe that has a 3'-ribonucleotide.

Figure 11A:
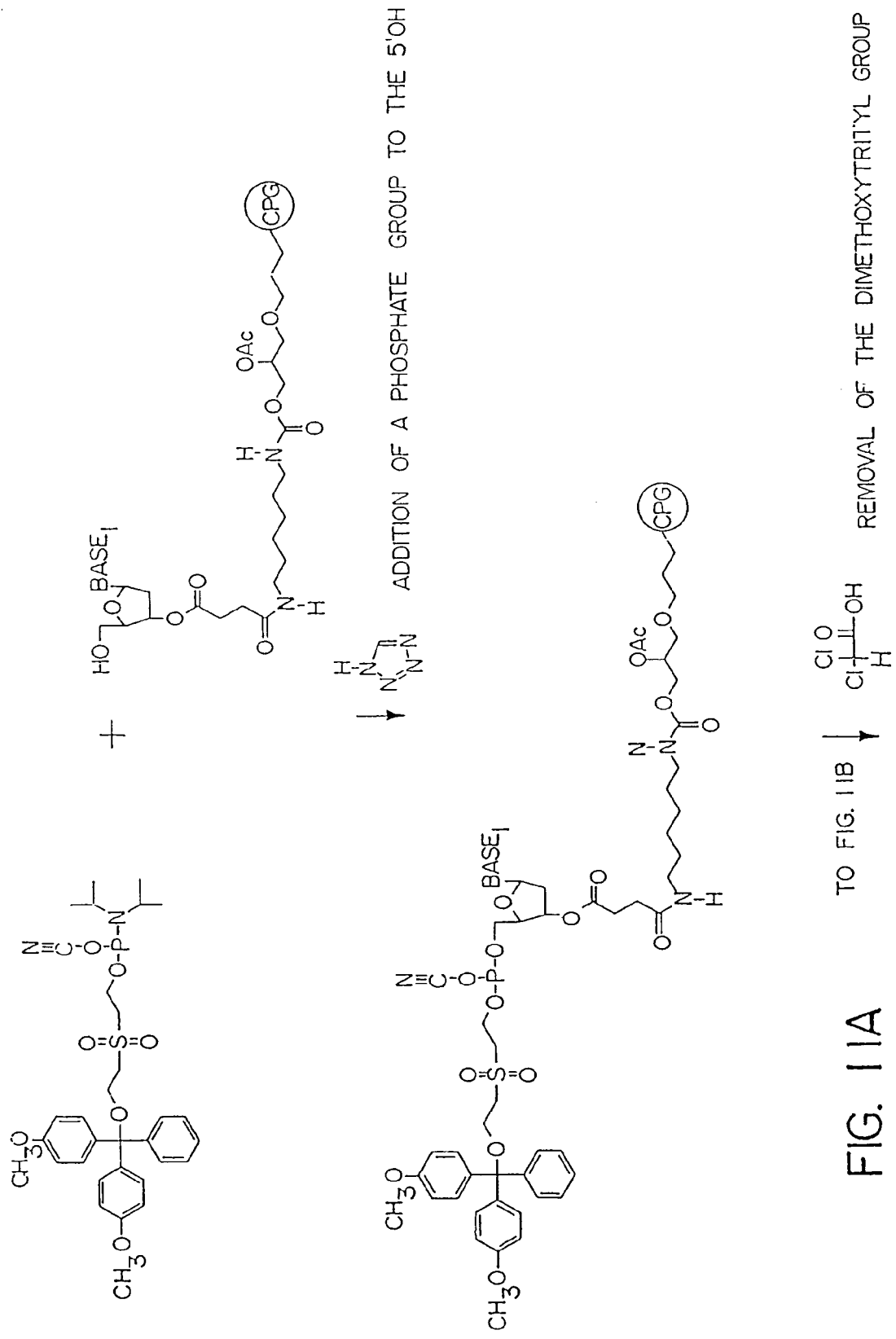

FIG. 11 is a schematic for labeling an oligonucleotide probe with biotin using a biotin phosphoramidite.

Figure 12:
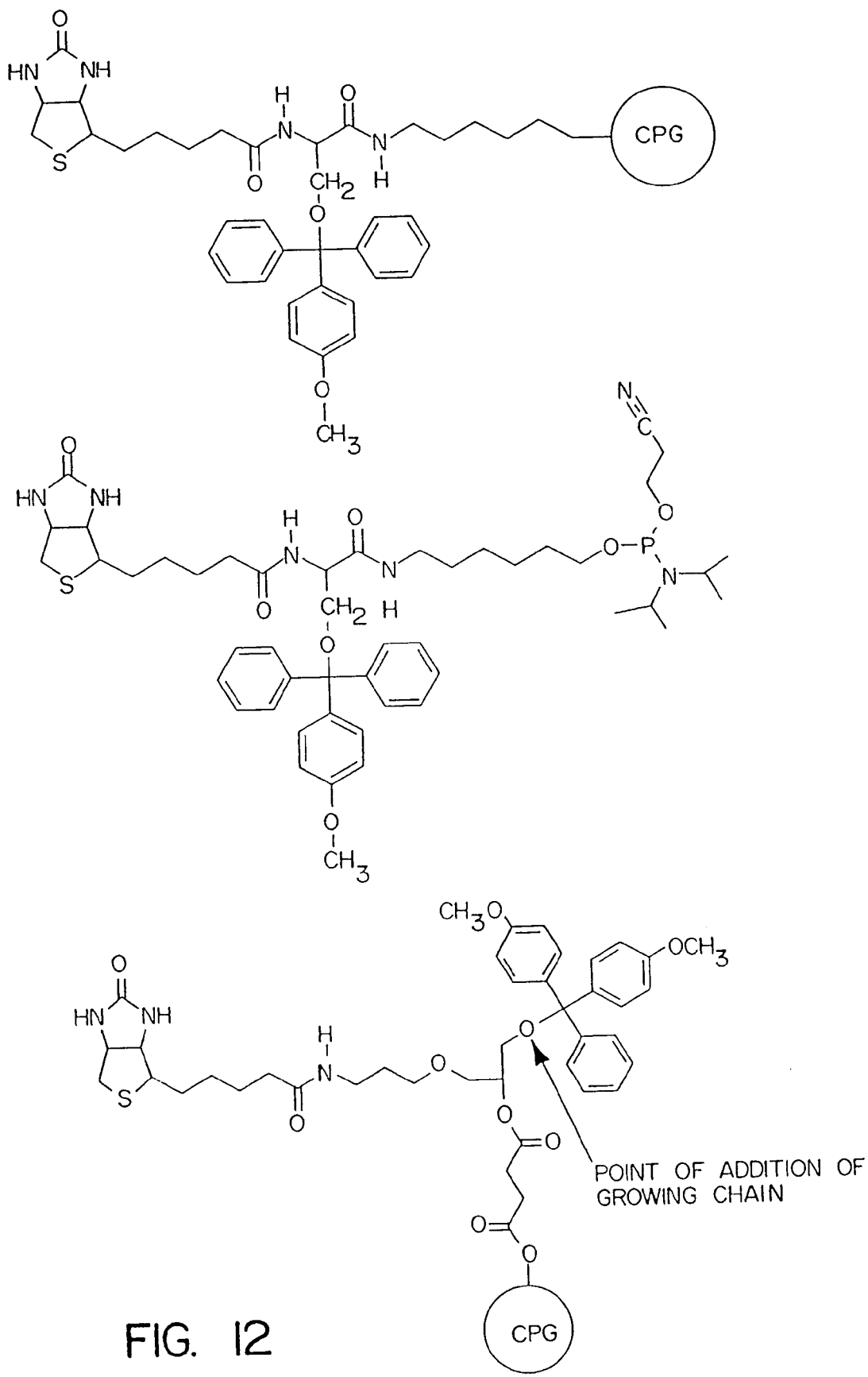

FIG. 12 shows a reagents for labeling oligonucleotide probes with biotin.

Figure 13:
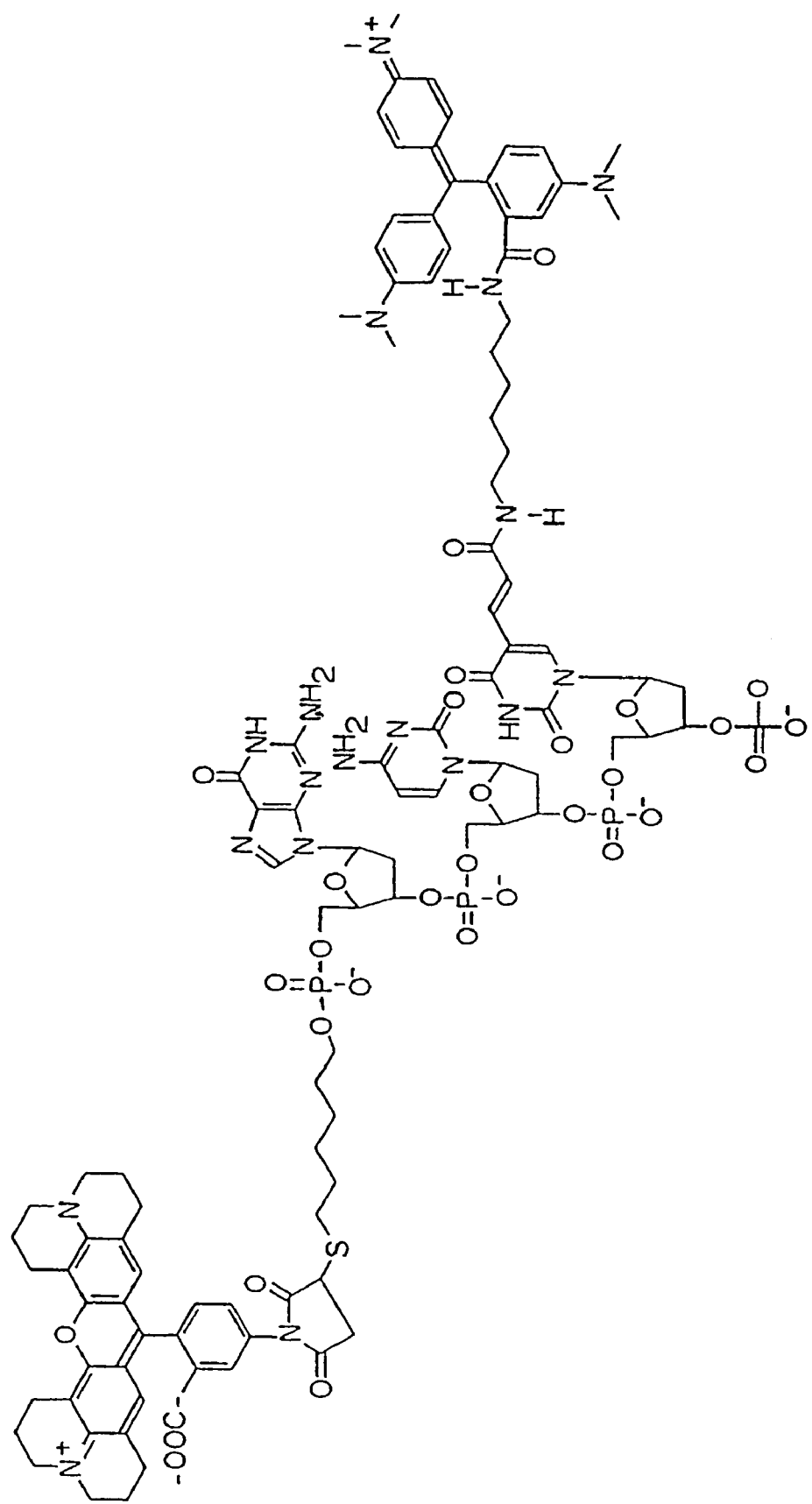

FIG. 13 shows an oligonucleotide probe labeled with rhodamine-X-590 and crystal violet.

Figure 14:
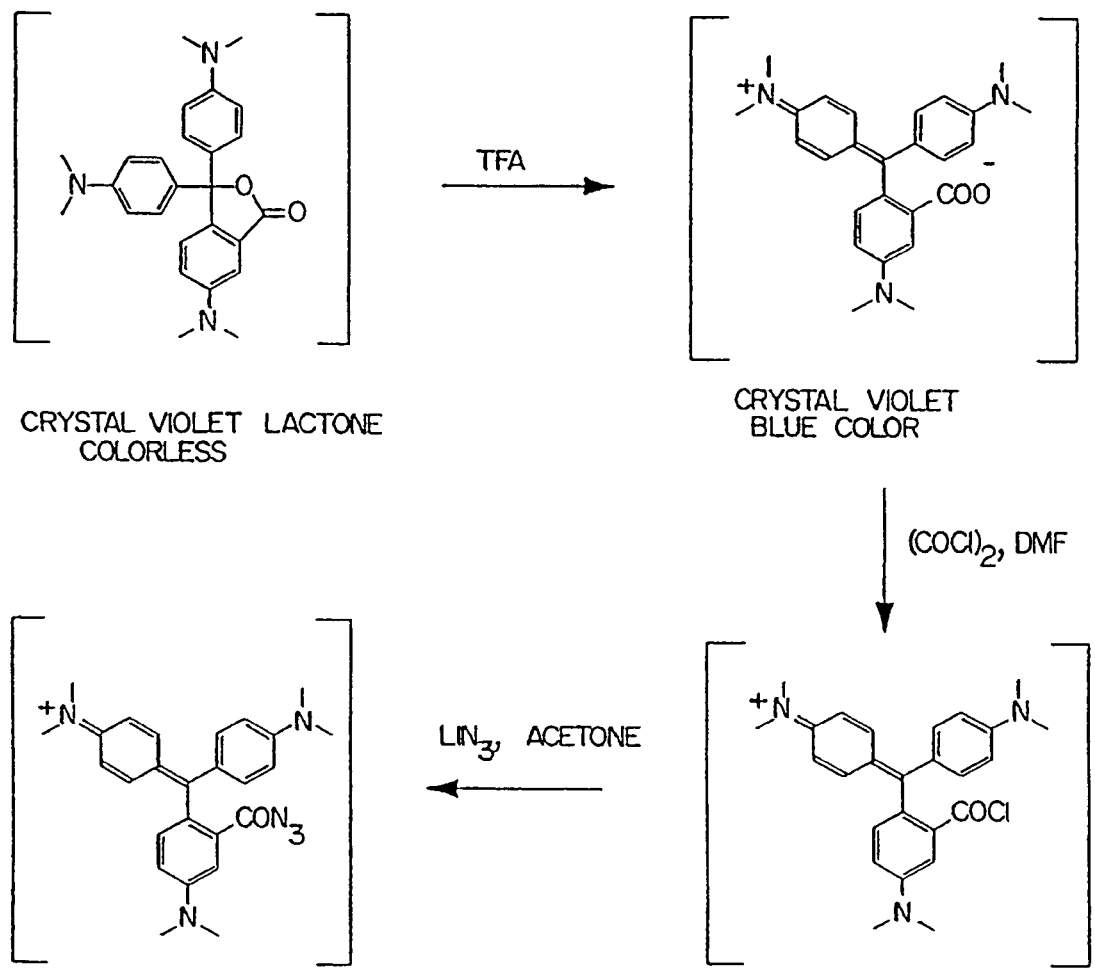

FIG. 14 shows a schematic for a reaction to generate an active acyl azide of crystal violet.

Figure 15:
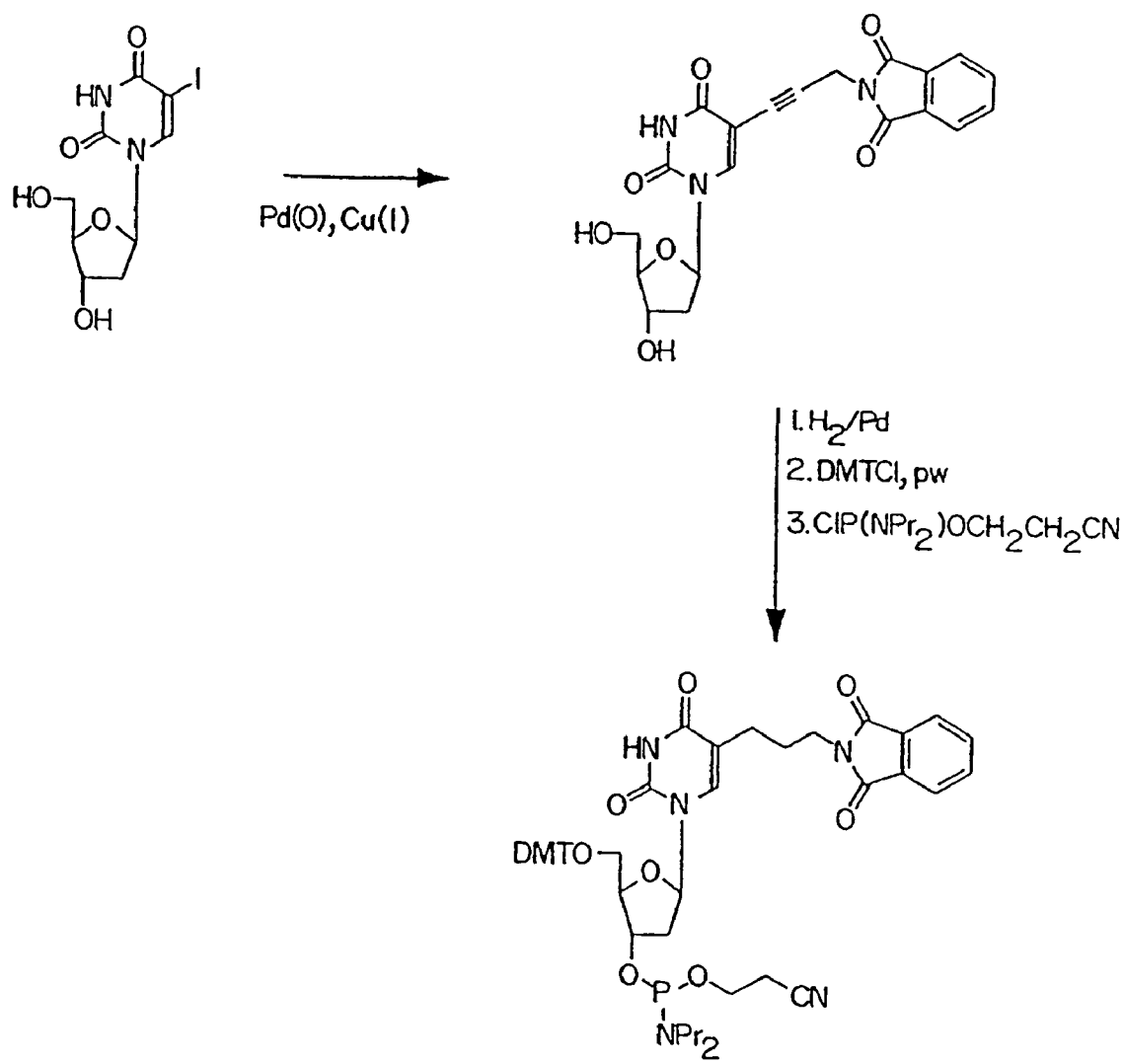

FIG. 15 shows a schematic for a reaction to add an amine to a thymidine for use in conjugating a label to an oligonucleotide probe.

Figure 16:
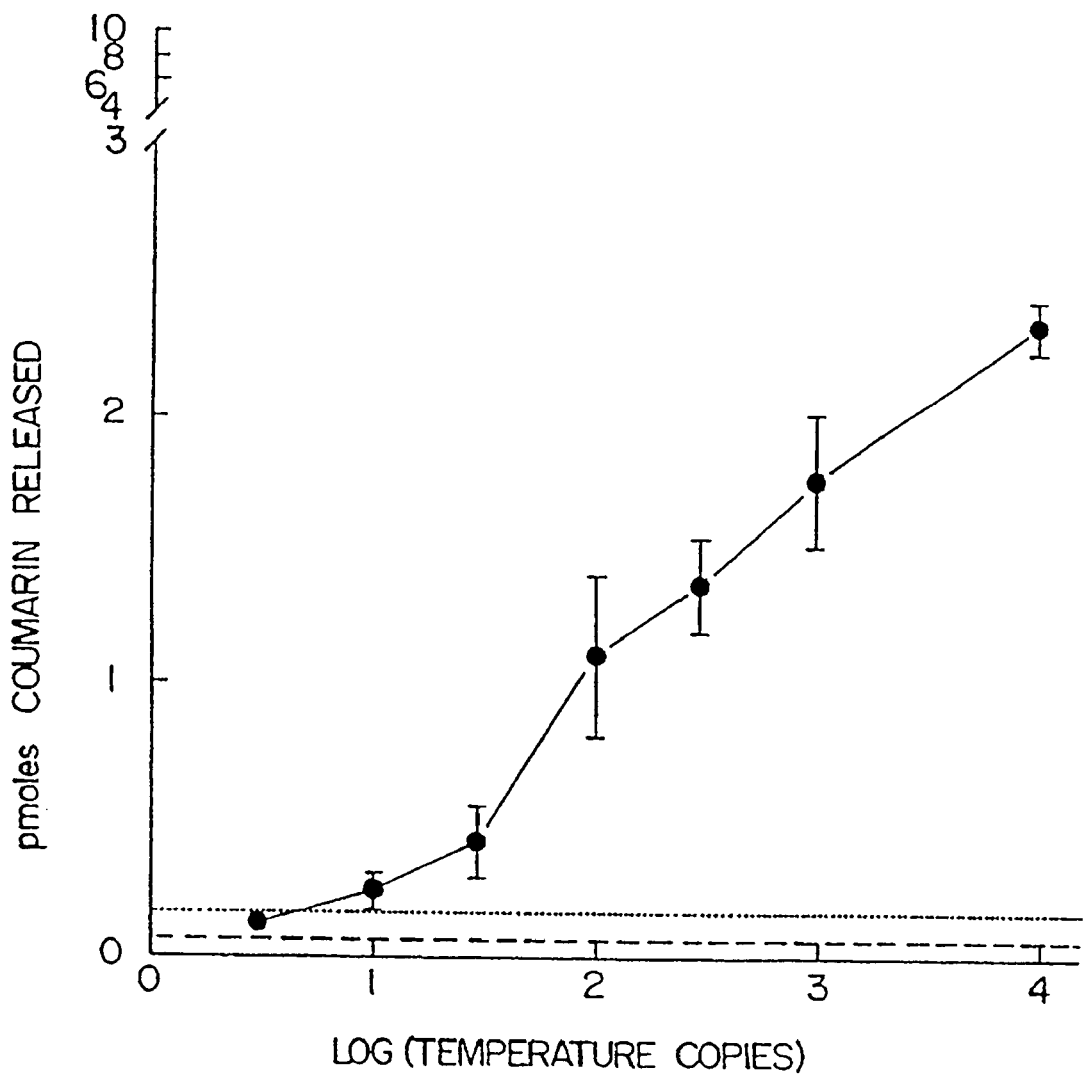

FIG. 16 shows typical results and relation of signal to input target number for the present method using Bakerbond™ PEI solid phase extractant.

As used herein, a "sample" refers to any substance containing or presumed to contain nucleic acid and includes a sample of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA. The oligonucleotide is comprised of a sequence of approximately at least 6 nucleotides, preferably at least about 10–12 nucleotides, and more preferably at least about 15–20 nucleotides corresponding to a region of the designated nucleotide sequence. "Corresponding" means identical to or complementary to the designated sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$." The $T_m$ of a particular nucleic acid duplex under specified conditions is the temperature at which half of the base pairs have disassociated.

As used herein, the term "target sequence" or "target nucleic acid sequence" refers to a region of the oligonucleotide which is to be either amplified, detected or both. The target sequence resides between the two primer sequences used for amplification.

As used herein, the term "probe" refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the polymerase chain reaction. Generally the 3' terminus of the probe will be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

As defined herein, "5'→3' nuclease activity" or "5' to 3'nuclease activity" refers to that activity of a template-specific nucleic acid polymerase including either a 5'→3' exonuclease activity traditionally associated with some DNA polymerases whereby nucleotides are removed from the 5' end of an oligonucleotide in a sequential manner, (i.e., E. coli DNA polymerase I has this activity whereas the Klenow fragment does not), or a 5'→3' endonuclease activity wherein cleavage occurs more than one phosphodiester bond (nucleotide) from the 5' end, or both.

The term "adjacent" as used herein refers to the positioning of the primer with respect to the probe on its complementary strand of the template nucleic acid. The primer and probe may be separated by 1 to about 20 nucleotides, more preferably, about 1 to 10 nucleotides, or may directly abut one another, as may be desirable for detection with a polymerization-independent process. Alternatively, for use in the polymerization-dependent process, as when the present method is used in the PCR amplification and detection methods as taught herein, the "adjacency" may be anywhere within the sequence to be amplified, anywhere downstream of a primer such that primer extension will position the polymerase so that cleavage of the probe occurs.

As used herein, the term "thermostable nucleic acid polymerase" refers to an enzyme which is relatively stable to heat when compared, for example, to nucleotide polymerases from E. coli and which catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. A representative thermostable enzyme isolated from *Thermus aquaticus* (Taq) is described in U.S. Pat. No. 4,889,818 and a method for using it in conventional PCR is described in Saiki et al., 1988, *Science* 239:487.

Taq DNA polymerase has a DNA synthesis-dependent, strand replacement 5'-3' exonuclease activity (see Gelfand, "Taq DNA Polymerase" in *PCR Technology: Principles and Applications for DNA Amplification*, Erlich, Ed., Stockton Press, N.Y. (1989), Chapter 2). In solution, there is little, if any, degradation of labeled oligonucleotides.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); and a series, *Methods in Enzymology* (Academic Press, Inc.). All patents, patent applications, and publications mentioned herein, both supra and infra, are hereby incorporated by reference.

The various aspects of the invention are based on a special property of nucleic acid polymerases. Nucleic acid polymerases can possess several activities, among them, a 5' to 3' nuclease activity whereby the nucleic acid polymerase can cleave mononucleotides or small oligonucleotides from an oligonucleotide annealed to its larger, complementary polynucleotide. In order for cleavage to occur efficiently, an upstream oligonucleotide must also be annealed to the same larger polynucleotide.

The 3' end of this upstream oligonucleotide provides the initial binding site for the nucleic acid polymerase. As soon as the bound polymerase encounters the 5' end of the downstream oligonucleotide, the polymerase can cleave mononucleotides or small oligonucleotides therefrom.

The two oligonucleotides can be designed such that they anneal in close proximity on the complementary target nucleic acid such that binding of the nucleic acid polymerase to the 3' end of the upstream oligonucleotide automatically puts it in contact with the 5' end of the downstream oligonucleotide. This process, because polymerization is not required to bring the nucleic acid polymerase into position to accomplish the cleavage, is called "polymerization-independent cleavage."

Alternatively, if the two oligonucleotides anneal to more distantly spaced regions of the template nucleic acid target, polymerization must occur before the nucleic acid polymerase encounters the 5' end of the downstream oligonucleotide. As the polymerization continues, the polymerase progressively cleaves mononucleotides or small oligonucleotides from the 5' end of the downstream oligonucleotide. This cleaving continues until the remainder of the downstream oligonucleotide has been destabilized to the extent that it dissociates from the template molecule. This process is called "polymerization-dependent cleavage."

In the present invention, a label is attached to the downstream oligonucleotide. Thus, the cleaved mononucleotides or small oligonucleotides which are cleaved by the 5'-3' nuclease activity of the polymerase can be detected.

Subsequently, any of several strategies may be employed to distinguish the uncleaved labeled oligonucleotide from the cleaved fragments thereof. In this manner, the present invention permits identification of those nucleic acid samples which contain sequences complementary to the upstream and downstream oligonucleotides.

The present invention exploits this 5' to 3' nuclease activity of the polymerase when used in conjunction with PCR. This differs from previously described PCR amplification wherein the post-PCR amplified target oligonucleotides are detected, for example, by hybridization with a probe which forms a stable duplex with that of the target sequence under stringent to moderately stringent hybridization and wash conditions. In contrast to those known detection methods used in post-PCR amplifications, the present invention permits the detection of the target nucleic acid sequences during amplification of this target nucleic acid. In the present invention, a labeled oligonucleotide is added concomitantly with the primer at the start of PCR, and the signal generated from hydrolysis of the labeled nucleotide(s) of the probe provides a means for detection of the target sequence during its amplification.

The present invention is compatible, however, with other amplification systems, such as the transcription amplification system, in which one of the PCR primers encodes a promoter that is used to make RNA copies of the target sequence. In similar fashion, the present invention can be used in a self-sustained sequence replication (3SR) system, in which a variety of enzymes are used to make RNA transcripts that are then used to make DNA copies, all at a single temperature. By incorporating a polymerase with 5'→3' exonuclease activity into a ligase chain reaction (LCR) system, together with appropriate oligonucleotides, one can also employ the present invention to detect LCR products.

Of course, the present invention can be applied to systems that do not involve amplification. In fact, the present invention does not even require that polymerization occur. One advantage of the polymerization-independent process lies in the elimination of the need for amplification of the target sequence. In the absence of primer extension, the target nucleic acid is substantially single-stranded. Provided the primer and labeled oligonucleotide are adjacently bound to the target nucleic acid, sequential rounds of oligonucleotide annealing and cleavage of labeled fragments can occur. Thus, a sufficient amount of labeled fragments can be generated, making detection possible in the absence of polymerization. As would be appreciated by those skilled in the art, the signal generated during PCR amplification could be augmented by this polymerization-independent activity.

In either process described herein, a sample is provided which is suspected of containing the particular oligonucleotide sequence of interest, the "target nucleic acid". The target nucleic acid contained in the sample may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denraturation involves temperatures ranging from about 80° C. to about 105° C., for times ranging from a few seconds to minutes. As an alternative to denaturation, the target nucleic acid may exist in a single-stranded form in the sample, such as, for example, single-stranded RNA or DNA viruses.

The denatured nucleic acid strands are then incubated with preselected oligonucleotide primers and labeled oligonucleotide (also referred to herein as "probe") under hybridization conditions, conditions which enable the binding of the primers and probes to the single nucleic acid strands. As known in the art, the primers are selected so that their relative positions along a duplex sequence are such that an extension product synthesized from one primer, when the extension product is separated from its template (complement), serves as a template for the extension of the other primer to yield a replicate chain of defined length.

Because the complementary strands are longer than either the probe or primer, the strands have more points of contact and thus a greater chance of finding each other over any given period of time. A high molar excess of probe, plus the primer, helps tip the balance toward primer and probe annealing rather than template reannealing.

The primer must be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the oligonucleotide primer typically contains about 15–30 nucleotides, although a primer may contain more or fewer nucleotides. The primers must be sufficiently complementary to anneal to their respective strands selectively and form stable duplexes.

The primers used herein are selected to be "substantially" complementary to the different strands of each specific sequence to be amplified. The primers need not reflect the exact sequence of the template, but must be sufficiently complementary to hybridize selectively to their respective strands. Non-complementary bases or longer sequences can be interspersed into the primer or located at the ends of the primer, provided the primer retains sufficient complementarity with a template strand to form a stable duplex therewith. The non-complementary nucleotide sequences of the primers may include restriction enzyme sites.

In the practice of the invention, the labeled oligonucleotide probe must be first annealed to a complementary nucleic acid before the nucleic acid polymerase encounters this duplex region, thereby permitting the 5' to 3' nuclease activity to cleave and release labeled oligonucleotide fragments.

To enhance the likelihood that the labeled oligonucleotide will have annealed to a complementary nucleic acid before primer extension polymerization reaches this duplex region, or before the polymerase attaches to the upstream oligonucleotide in the polymerization-independent process, a variety of techniques may be employed. For the polymerization-dependent process, one can position the probe so that the 5'-end of the probe is relatively far from the 3'-end of the primer, thereby giving the probe more time to anneal before primer extension blocks the probe binding site. Short primer molecules generally require lower temperatures to form sufficiently stable hybrid complexes with the target nucleic acid. Therefore, the labeled oligonucleotide can be designed to be longer than the primer so that the labeled oligonucleotide anneals preferentially to the target at higher temperatures relative to primer annealing.

One can also use primers and labeled oligonucleotides having differential thermal stability. For example, the nucleotide composition of the labeled oligonucleotide can be chosen to have greater G/C content and, consequently, greater thermal stability than the primer. In similar fashion, one can incorporate modified nucleotides into the probe, which modified nucleotides contain base analogs that form more stable base pairs than the bases that are typically present in naturally occurring nucleic acids.

Modifications of the probe that may facilitate probe binding prior to primer binding to maximize the efficiency of the present assay include the incorporation of positively charged or neutral phosphodiester linkages in the probe to decrease the repulsion of the polyanionic backbones of the probe and target (see Letsinger et al., 1988, *J. Amer. Chem. Soc.* 110:4470); the incorporation of alkylated or halogenated bases, such as 5-bromouridine, in the probe to increase base stacking; the incorporation of ribonucleotides into the probe to force the probe:target duplex into an "A" structure, which has increased base stacking; and the substitution of 2,6-diaminopurine (amino adenosine) for some or all of the adenosines in the probe. In preparing such modified probes of the invention, one should recognize that the rate limiting step of duplex formation is "nucleation," the formation of a single base pair, and therefore, altering the biophysical characteristic of a portion of the probe, for instance, only the 3' or 5' terminal portion, can suffice to achieve the desired result. In addition, because the 3' terminal portion of the probe (the 3' terminal 8 to 12 nucleotides) dissociates following exonuclease degradation of the 5' terminus by the polymerase, modifications of the 3' terminus can be made without concern about interference with polymerase/nuclease activity.

The thermocycling parameters can also be varied to take advantage of the differential thermal stability of the labeled oligonucleotide and primer. For example, following the denaturation step in thermocycling, an intermediate temperature may be introduced which is permissible for labeled oligonucleotide binding but not primer binding, and then the temperature is further reduced to permit primer annealing and extension. One should note, however, that probe cleavage need only occur in later cycles of the PCR process for suitable results. Thus, one could set up the reaction mixture so that even though primers initially bind preferentially to probes, primer concentration is reduced through primer extension so that, in later cycles, probes bind preferentially to primers.

To favor binding of the labeled oligonucleotide before the primer, a high molar excess of labeled oligonucleotide to primer concentration can also be used. In this embodiment, labeled oligonucleotide concentrations are typically in the range of about 2 to 20 times higher than the respective primer concentration, which is generally $0.5-5\times10^{-7}$ M. Those of skill recognize that oligonucleotide concentration, length, and base composition are each important factors that affect the $T_m$ of any particular oligonucleotide in a reaction mixture. Each of these factors can be manipulated to create a thermodynamic bias to favor probe annealing over primer annealing.

The oligonucleotide primers and labeled oligonucleotides may be prepared by any suitable method. Methods for preparing oligonucleotides of specific sequence are known in the art, and include, for example, cloning and restriction of appropriate sequences and direct chemical synthesis. Chemical synthesis methods may include, for example, the phosphotriester method described by Narang et al., 1979, *Methods in Enzymology* 68:90, the phosphodiester method disclosed by Brown et al., 1979, *Methods in Enzymology* 68:109, the diethylphosphoramidate method disclosed in Beaucage et al., 1981, *Tetrahedron Letters* 22:1859, and the solid support method disclosed in U.S. Pat. No. 4,458,066.

The composition of the labeled oligonucleotide can be designed to favor nuclease activity over strand displacement (mono- and dinucleotide fragments over oligonucleotides) by means of choice of sequences that are GC-rich or that avoid sequential A's and T's and by choice of label position in the probe. In the presence of AT-rich sequences in the 5' complementary probe region, cleavage occurs after the approximately fourth, fifth or sixth nucleotide. However, in a CC-rich 5' complementary probe region, cleavage generally occurs after the first or second nucleotide. Alternatively, the incorporation of modified phosphodiester linkages (e.g., phosphorothioate or methylphosphonates) in the labeled probe during chemical synthesis (Noble et al., 1984, *Nuc Acids Res* 12:3387–3403; Iyer et al., 1990, *J. Am. Chem. Soc.* 112:1253–1254) may be used to prevent cleavage at a selected site. Depending on the length of the probe, the composition of the 5' complementary region of the probe, and the position of the label, one can design a probe to favor preferentially the generation of short or long labeled probe fragments for use in the practice of the invention.

The oligonucleotide is labeled, as described below, by incorporating moieties detectable by spectroscopic, photochemical, biochemical, immunochemical, or chemical means. The method of linking or conjugating the label to the oligonucleotide probe depends, of course, on the type of label(s) used and the position of the label on the probe.

A variety of labels that would be appropriate for use in the invention, as well as methods for their inclusion in the probe, are known in the art and include, but are not limited to,.enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), ligands having specific binding partners, or any other labels that may interact with each other to enhance, alter, or diminish a signal. Of course, should the PCR be practiced using a thermal cycler instrument, the label must be able to survive the temperature cycling required in this automated process.

Among radioactive atoms, $^{32}P$ is preferred. Methods for introducing $^{32}P$ into nucleic acids are known in the art, and include, for example, 5' labeling with a kinase, or random insertion by nick translation. Enzymes are typically detected by their activity. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. For example, $^{125}$I may serve as a radioactive label or as an electron-dense reagent. HRP may serve as enzyme or as antigen for a monoclonal antibody. Further, one may combine various labels for desired effect. For example, one might label a probe with biotin, and detect the presence of the probe with avidin labeled with $^{125}$I, or with an anti-biotin monoclonal antibody labeled with HRP. Other permutations and possibilities will be readily apparent to those of ordinary skill in the art and are considered as equivalents within the scope of the instant invention.

Fluorophores for use as labels in constructing labeled probes of the invention include rhodamine and derivatives, such as Texas Red, fluorescein and derivatives, such as 5-bromomethyl fluorescein, Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromotrimethyl-ammoniobimane. In general, fluorophores with wide Stokes shifts are preferred, to allow using fluorimeters with filters rather than a monochromometer and to increase the efficiency of detection.

In some situations, one can use two interactive labels on a single oligonucleotide with due consideration given for maintaining an appropriate spacing of the labels on the oligonucleotide to permit the separation of the labels during oligonucleotide hydrolysis. Rhodamine and crystal violet are preferred interactive labels.

In another embodiment of the invention, detection of the hydrolyzed labeled probe can be accomplished using, for example, fluorescence polarization, a technique to differentiate between large and small molecules based on molecular tumbling. Large molecules (e.g., intact labeled probe) tumble in solution much more slowly than small molecules. Upon linkage of a fluorescent moiety to the molecule of interest (e.g., the 5' end of a labeled probe), this fluorescent moiety can be measured (and differentiated) based on molecular tumbling, thus differentiating between intact and digested probe. Detection may be measured directly during PCR or may be performed post PCR.

In yet another embodiment, two labelled oligonucleotides are used, each complementary to separate regions of separate strands of a double-stranded target region, but not to each other, so that an oligonucleotide anneals downstream of each primer. For example, the presence of two probes can potentially double the intensity of the signal generated from a single label and may further serve to reduce product strand reannealing, as often occurs during PCR amplification. The probes are selected so that the probes bind at positions adjacent (downstream) to the positions at which primers bind.

One can also use multiple probes in the present invention to achieve other benefits. For instance,-one could test for any number of pathogens in a sample simply by putting as many probes as desired into the reaction mixture; the probes could each comprise a different label to facilitate detection.

One can also achieve allele-specific or species-specific (i.e., specific for the different species of *Borrelia*, the causative agent of Lyme disease) discrimination using multiple probes in the present invention, for instance, by using probes that have different T$_m$s and conducting the annealing/cleavage reaction at a temperature specific for only one probe/ allele duplex. For instance, one can choose a primer pair that amplifies both HTLVI and HTLVII and use two probes, each labeled uniquely and specific for either HTLVI or HTLVII. One can also achieve allele specific discrimination by using only a single probe and examining the types of cleavage products generated. In this embodiment of the invention, the probe is designed to be exactly complementary, at least in the 5' terminal region, to one allele but not to the other allele(s). With respect to the other allele(s), the probe will be mismatched in the 5' terminal region of the probe so that a different cleavage product will be generated as compared to the cleavage product generated when the probe is hybridized to the exactly complementary allele.

Although probe sequence can be selected to achieve important benefits, one can also realize important advantages by selection of probe label(s). The labels may be attached to the oligonucleotide directly or indirectly by a variety of techniques. Depending on the precise type of label used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5' or the 3' terminus via an appropriately protected phosphoramidite, and can label them using protocols described in, for example, *PCR Protocols: A Guide to Methods and Applications* (Innis et al., eds. Academic Press, Inc., 1990).

Methods for introducing oligonucleotide functionalizing reagents to introduce one or more sulfhydryl, amino or hydroxyl moieties into the oligonucleotide probe sequence, typically at the 5' terminus, are described in U.S. Pat. No. 4,914,210. A 5' phosphate group can be introduced as a radioisotope by using polynucleotide kinase and gamma-$^{32}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into an oligonucleotide probe. Similarly, etheno-dC or 2-amino purine deoxyriboside is another analog that could be used in probe synthesis. The probes containing such nucleotide derivatives may be hydrolyzed to release much more strongly fluorescent mononucleotides by the 5' to 3' nuclease activity as DNA polymerase extends a primer during PCR.

Template-dependent extension of the oligonucleotide primer(s) is catalyzed by a polymerizing agent in the presence of adequate amounts of the four deoxyribonucleoside triphosphates (dATP, dGTP, dCTP, and dTTP) or analogs as discussed above, in a reaction medium comprised of the appropriate salts, metal cations, and pH buffering system. Suitable polymerizing agents are enzymes known to catalyze primer- and template-dependent DNA synthesis and possess the 5' to 3' nuclease activity. Known DNA polymerases include, for example, *E. coli* DNA polymerase I, *Thermus thermophilus* (Tth) DNA polymerase, *Bacillus stearothermophilus* DNA polymerase, *Thermococcus litoralis* DNA polymerase, and *Thermus aquaticus* (Taq) DNA polymerase. The reaction conditions for catalyzing DNA synthesis with these DNA polymerases are well known in the art. To be useful in the present invention, the polymerizing agent must efficiently cleave the oligonucleotide and release labeled fragments so that the signal is directly or indirectly generated.

The products of the synthesis are duplex molecules consisting of the template strands and the primer extension strands, which include the target sequence. Byproducts of this synthesis are labeled oligonucleotide fragments that consist of a mixture of mono-, di- and larger nucleotide fragments. Repeated cycles of denaturation, labeled oligonucleotide and primer annealing, and primer extension and cleavage of the labeled oligonucleotide result in the exponential accumulation of the target region defined by the primers and the exponential generation of labeled fragments. Sufficient cycles are run to achieve a detectable species of label, which can be several orders of magnitude greater than background signal, although in common practice such high ratios of signal to noise may not be achieved or desired.

In a preferred method, the PCR process is carried out as an automated process that utilizes a thermostable enzyme. In this process the reaction mixture is cycled through a denaturing step, a probe and primer annealing step, and a synthesis step, whereby cleavage and displacement occurs simultaneously with primer-dependent template extension. A DNA thermal cycler, such as the commercially available machine from Perkin-Elmer Cetus Instruments, which is specifically designed for use with a thermostable enzyme, may be employed.

Temperature stable polymerases are preferred in this automated process, because the preferred way of denaturing the double stranded extension products is by exposing them to a high temperature (about 95° C.) during the PCR cycle. For example, U.S. Pat. No. 4,889,818 discloses a representative thermostable enzyme isolated from *Thermus aquaticus*. Additional representative temperature stable polymerases include, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus litoralis,* and *Methanothermus fervidus*.

Detection or verification of the labeled oligonucleotide fragments may be accomplished by a variety of methods and may be dependent on the source of the label or labels employed. One convenient embodiment of the invention is to subject the reaction products, including the cleaved labeled fragments, to size analysis. Methods for determining the size of the labeled nucleic acid fragments are known in the art, and include, for example, gel electrophoresis, sedimentation in gradients, gel exclusion chromatography and homochromatography.

During or after amplification, separation of the labeled fragments from the PCR mixture can be accomplished by, for example, contacting the PCR mixture with a solid phase extractant (SPE). For example, materials having an ability to bind oligonucleotides on the basis of size, charge, or interaction with the oligonucleotide bases can be added to the PCR mixture, under conditions where labeled, uncleaved oligonucleotides are bound and short, labeled fragments are not. Such SPE materials include ion exchange resins or beads, such as the commercially available binding particles Nensorb (DuPont Chemical Co.), Nucleogen (The Nest Group), PEI, BakerBond™ PEI, Amicon PAE 1,000, Selectacel™ PEI, Boronate SPE with a 3'-ribrose probe, SPE containing sequences complementary to the 3'-end of the probe, and hydroxylapatite. In a specific embodiment, if a dual labeled oligonucleotide comprising a 3' biotin label separated from a 5' label by a nuclease susceptible cleavage site is employed as the signal means, the PCR amplified mixture can be contacted with materials containing a specific binding partner such as avidin or streptavidin, or an antibody or monoclonal antibody to biotin. Such materials can include beads and particles coated with specific binding partners and can also include magnetic particles.

Following the step in which the PCR mixture has been contacted with an SPE, the SPE material can be removed by filtration,.sedimentation, or magnetic attraction, leaving the labeled fragments free of uncleaved labeled oligonucleotides and available for detection.

Reagents employed in the methods of the invention can be packaged into diagnostic kits. Diagnostic kits include the labeled oligonucleotides and the primers in separate containers. If the oligonucleotide is unlabeled, the specific labeling reagents may also be included in the kit. The kit may also contain other suitably packaged reagents and materials needed for amplification, for example, buffers, dNTPs, and/or polymerizing means, and for detection analysis, for example, enzymes and solid phase extractants, as well as instructions for conducting the assay.

The examples presented below are intended to be illustrative of the various methods and compounds of the invention.

EXAMPLE 1

PCR Probe Label Release

A PCR amplification was performed which liberated the 5' $^{32}$P-labeled end of a complementary probe when specific intended product was synthesized.

A. Labeling of Probe with Gamma-$^{32}$P-ATP and Polynucleotide Kinase

Ten pmol of each probe (BW31, BW33, BW35, sequences provided below) were individually mixed with fifteen units of T4 polynucleotide kinase (New England Biolabs) and 15.3 pmol of gamma-$^{32}$P-ATP (New England Nuclear, 3000 Ci/mmol) in a 50 µl reaction volume containing 50 mM Tris-HCl, pH 7.5, 10 mM MgCl$_2$, 5 mM dithiothreitol, 0.1 mM spermidine and 0.1 mM EDTA for 60 minutes at 37° C. The total volume was then phenol/chloroform extracted, and ethanol precipitated as described by Sambrook et al., *Molecular Cloning*, Second Edition (1989). Probes were resuspended in 100 µl of TE buffer and run over a Sephadex G-50 spin dialysis column to remove unincorporated gamma-$^{32}$P-ATP as taught in Sambrook et al., supra. TCA precipitation of the reaction products indicated the following specific activities:

BW31: 1.98×10$^6$ cpm/pmol
BW33: 2.54×10$^6$ cpm/pmol
BW35: 1.77×10$^6$ cpm/pmol Final concentration of all three probes was 0.10 pmol/µl.

B. Amplification

The amplified region was a 350 base pair product from the bacteriophage M13mp10w directed by primers BW36 and BW42. The region of each numbered primer sequence designated herein, follows standard M13 nucleotide sequence usage.

```
SEQ ID NO: 1 BW36 = 5' 5241-5268 3'
             5'-CCGATAGTTTGAGTTCTTCTACTCAGGC-3'

SEQ ID NO: 2 BW42 = 5' 5591-5562 3'
             5'-GAAGAAAGCGAAAGGAGCGGGCGCTAGGGC-3'
```

Three different probes were used; each contained the 30 base exactly complementary sequence to M13mp10w but differed in the lengths of non-complementary 5' tail regions.

Probes were synthesized to have a 3'-PO$_4$ instead of a 3'-OH to block any extension by Taq polymerase.

```
SEQ ID NO: 3 BW31 = 5' 5541-5512 3'
            5'CGCTGCGCGTAACCACCACACCCGCCGCGCX-3'

SEQ ID NO: 4 BW33 = 5' 5541-5512 3'
            5'-*gatCGCTGCGCGTAACCACCACACCCGC-
            CGCCGCGCX-3'

SEQ ID NO: 5 BW35 = 5' 5541-5512 3'
            5'-*cgtcaccgatCGCTGCGCGTAACCACCA-
            CACCCGCCGCGCX-3'
X = 3'-phosphate
a, t, g, c, = bases non-complementary to template
strand
* = gammaa ³²P-ATP label
```

For amplification of the 350 bp fragment, $10^{-3}$ pmol of target M13mp10w sequence were added to a 50 µl reaction volume containing 50 mM KCl, 10 mM Tris-HCl, pH 8.3, 3 mM MgCl$_2$, 10 pmol each of primers BW36 and BW42, 200 µM each of the four deoxyribonucleoside triphosphates, 1.25 units Taq DNA polymerase, and either 1, 10 or 20 pmol of isotopically diluted probe BW31, BW33 or BW35. The amount of radiolabeled probe was held constant at 0.4 pmol per reaction and diluted to 1, 10 or 20 pmol with nonradioactive probe. Taq polymerase was added at 4 µl per reaction at 0.3125 U/µl and diluted in 10 mM Tris-HCl, pH 8.0, 50 mM KCl, 0.1 mM EDTA, 0.5% NP40, 0.5% Tween 20, and 500 µg/ml gelatin.

A master reaction mix was made containing appropriate amounts of reaction buffer, nucleoside triphosphates, both primers and enzyme. From this master mix aliquots were taken and to them were added template and various concentrations of each probe. Control reactions consisted of adding all reaction components except template, and all reaction components except probe. Each reaction mixture was overlayed with 50 µl of mineral oil to prevent evaporation, microcentrifuged for 45 seconds, and then placed into a thermal cycler. Reaction mixtures were subjected to the following amplification scheme:

| Fifteen cycles: | 96° C. denaturation, 1 min |
| --- | --- |
|  | 60° C. anneal/extension, 1.5 min |
| One cycle: | 96° C. denaturation, 1 min |
|  | 60° C. anneal/extension, 5.5 min |

After cycling, the mineral oil was extracted with 50 µl of chloroform, the mixtures were stored at 4° C., and the following tests were performed.

C. Analysis

For acrylamide gel analysis, 4 µl of each amplification reaction were mixed with 3 µl of 5× gel loading mix (0.125% bromophenol blue, 12.5% Ficoll 400 in H$_2$O) and loaded onto a 4% acrylamide gel (10 ml of 10× TBE buffer, 1 ml of 10% ammonium persulfate, 10 ml of 40% Bis Acrylamide 19:1, 50 µl of TEMED, and 79 ml of H$_2$O) in 1× TBE buffer (0.089 M Tris, 0.089 M boric acid, and 2 mM EDTA) and electrophoresed for 90 minutes at 200 volts. After staining with ethidium bromide, DNA was visualized by UV fluorescence.

The results showed that the presence of each of these three probes at the various concentrations had no effect on the amount of amplified product generated. Sample lanes containing no probe showed discrete high intensity 350 base pair bands corresponding to the desired sequence. All lanes containing probe showed the same, as well as a few faint bands at slightly higher molecular weight. Control lanes without template added showed no bands whatsoever at 350 bases, only lower intensity bands representing primer at 30–40 bases.

After photographing, the gel was transferred onto Whatman paper, covered with Saran Wrap and autoradiographed. An overnight exposure revealed that 90–95% of the radiolabel was near the bottom of the gel, where probe or partially degraded probe would run.

For the denaturing gel analysis, 2 µl of each amplification reaction were mixed with 2 µl of formamide loading buffer (0.2 ml of 0.5 M EDTA pH 8, 10 mg of bromophenol blue, 10 mg of xylene cyanol, and 10 ml of formamide), then heated to 96° C. for 3–5 min and placed on ice. Samples were loaded onto a 6.2% denaturing gradient polyacrylamide gel (7 M urea with both a sucrose and a buffer gradient) according to the procedure of Sambrook et al., supra. The gel was electrophoresed for 90 minutes at 2000 V, 45 W, then transferred onto Whatman paper and autoradiographed.

Results from the denaturing gel indicated that about 50% of each probe was degraded into smaller labeled fragments. Approximately 50%–60% of the counts lie in the 30–40 base range, corresponding to undergraded probe. A very faint band is visible at 300 bases for all the amplification reactions, suggesting that a very small percentage of the probes have lost, or never had, a 3'-PO$_4$ group and have been extended. The remainder of the counts are in the range of zero to fifteen bases The resolution on such a gel does not reveal the exact size of products, which can be better determined by homochromatography analysis.

For a homochromatography analysis, 1 µl of each sample was spotted 1.2 cm apart onto a Polygram CEL 300 DEAE 20×20 cm cellulose thin layer plate, which was pre-spotted with 5 µl of sheared herring sperm DNA (150 µg/ml) and allowed to dry. After the sample was dried, the plate was placed in a trough with distilled H$_2$O, and the water allowed to migrate just above the sample loading area. The plate was then placed in a glass development tank containing filtered Homo-mix III (Jay et al., 1979, *Nuc. Acid Res.* 1(3):331–353), a solution of partially hydrolized RNA containing 7 M urea, in a 70° C. oven. The Homo-Mix was allowed to migrate by capillary action to the top of the plate, at which time the plate was removed, allowed to dry, covered with Saran Wrap, and then autoradiographed.

Figure 1:
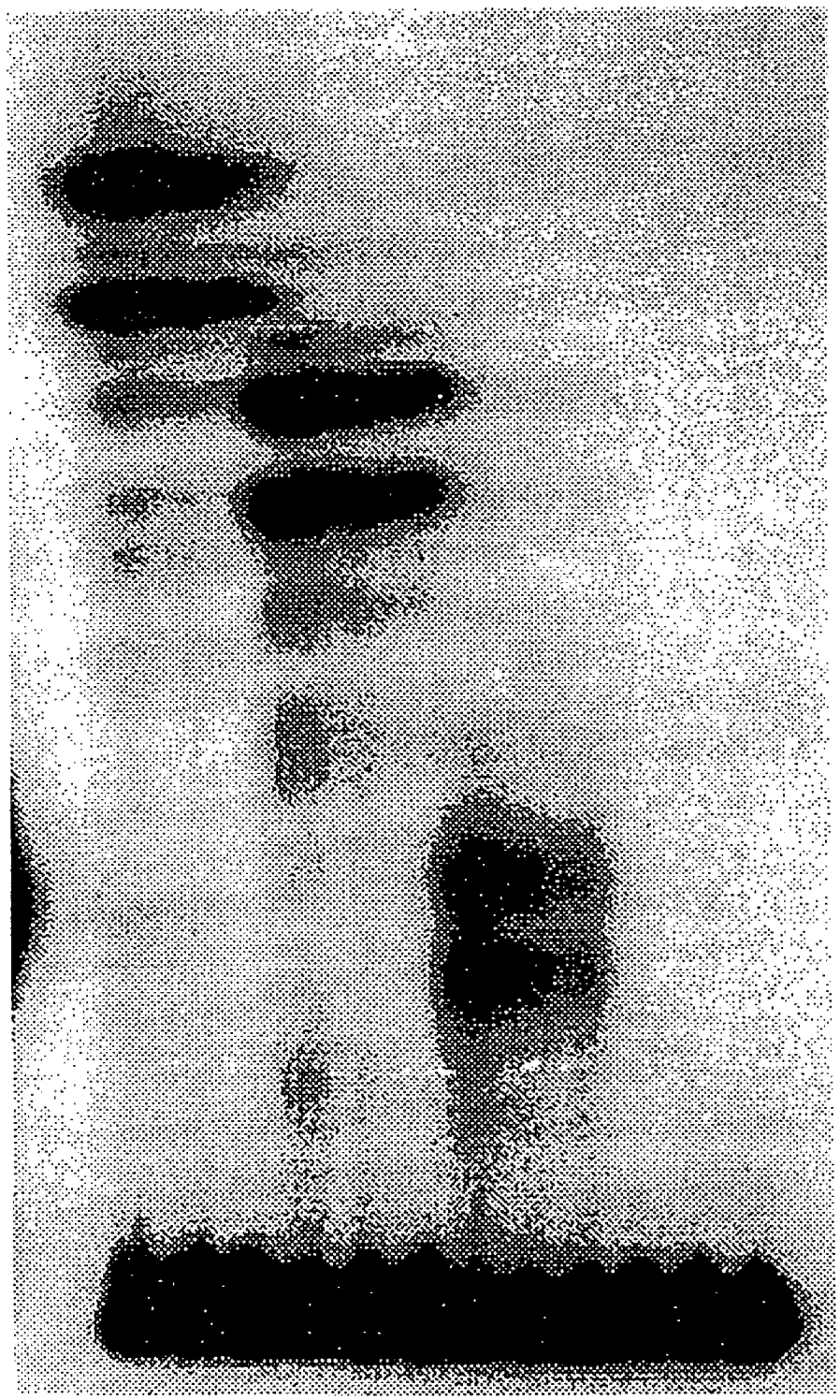
FIG. 1 is an autoradiograph of a DEAE cellulose thin layer chromatography (TLC) plate illustrating the release of labeled fragments from cleaved probe.

An overnight exposure of the homochromatography plate also indicated that about 40% of the probes were degraded into smaller fragments. These fragments were very specific in size, depending upon the length of the 5' non-complementary tail of each probe. FIG. 1 shows an autoradiograph of the TLC plate. Probe BW31 (Lanes 1–3), which was fully complementary to the M13mp10w template, generated labeled fragments predominantly one to two bases long. Probe BW33, (Lanes 4–6), containing a 5' 3 base non-complementary region, released products predominantly four to six bases long. BW35 (Lanes 7–9) had a 5' 10 base non-complementary tail and released products predominantly 12 to 13 bases in length. Lanes 10–12 are control reactions containing either BW31, BW33 or BW35 and all PCR components except template after 15 cycles. During DNA synthesis, the enzyme displaced the first one or two paired bases encountered and then cut at that site, indicative of an endonuclease-like activity. The results show specific probe release coordinately with product accumulation in PCR.

EXAMPLE 2

Specificity of Probe Label Release

The specificity of labeled probe release was examined by performing a PCR amplification using bacteriophage lambda DNA and primers, and a series of non-complementary kinased probes.

The region to be amplified was a 500 nucleotide region on bacteriophage lambda DNA from the GeneAmp® DNA Amplification Reagent kit (Perkin-Elmer Cetus), flanked by primers PCRO1 and PCRO2, also from the GeneAmp® DNA kit.

```
SEQ ID NO: 6   PCRO1 = 5' 7131-7155 3'
               5'-GATGAGTTCGTGTCCGTACAACTGG-3'

SEQ ID NO: 7   PCRO2 = 5' 7630-7606 3';
               5'-GGTTATCGAAATCAGCCACAGCGCC-3'
```

Aliquots of the same three labeled probes BW31, BW33 and BW35 identified in Example I, were used, all of which were entirely non-complementary to the target sequence.

For amplification of the 500 base pair region, 0.5 ng of target lambda DNA sequence (control Template, Lot #3269, 1 µg/ml, dilute 1:10 in 10 mM Tris-HCl pH 8.0, 1 mM EDTA, and 10 mM NaCl for stock) were added to a 50 µl reaction volume containing 50 mM KCl, 10 mM Tris-HCl, pH 8.3, 3 mM $MgCl_2$, 1 µM each of primers PCRO1 (Lot #3355) and PCRO2 (Lot #3268), 200 µM each of four deoxynucleoside triphosphates, 1.25 units Taq DNA polymerase, and either 2, 10 or 20 pmol of isotopically diluted probe BW31, BW33 or BW35. The amount of radiolabeled probe was held constant to 0.4 pmol per reaction and diluted to 1, 10 or 20 pmol with nonradioactive probe. Taq DNA polymerase was added at 4 µl per reaction at 0.3125 units/µl and diluted in 10 mM Tris-HCl pH 8.0, 50 mM KCl, 0.1 mM EDTA, 0.5% NP40, 0.5% Tween 20, and 500 µg/ml gelatin.

The master reaction mix was made as previously taught, along with the control reactions minus probe or minus enzyme. The reaction mixtures were amplified following the cycling conditions set forth in Example 1B and then analyzed as follows. For acrylamide gel analysis, 4 µl of each amplification reaction mixed with 3 µl of 5× loading mix were loaded onto a 4% acrylamide gel in 1×TBE buffer and electrophoresed for 90 minutes at 200 volts. After staining with ethidium bromide, DNA was visualized by UV fluorescence.

The results show that the presence of any probe at any concentration has no effect on the amount of amplified product generated. Sample control lanes containing no probe, and all lanes containing probe, showed a discrete high intensity 500 base pair band corresponding to the desired sequence. Control lanes with no enzyme added did not show any product bands but only low intensity bands representing primer and probe of approximately 30–40 nucleotides.

Figure 2:
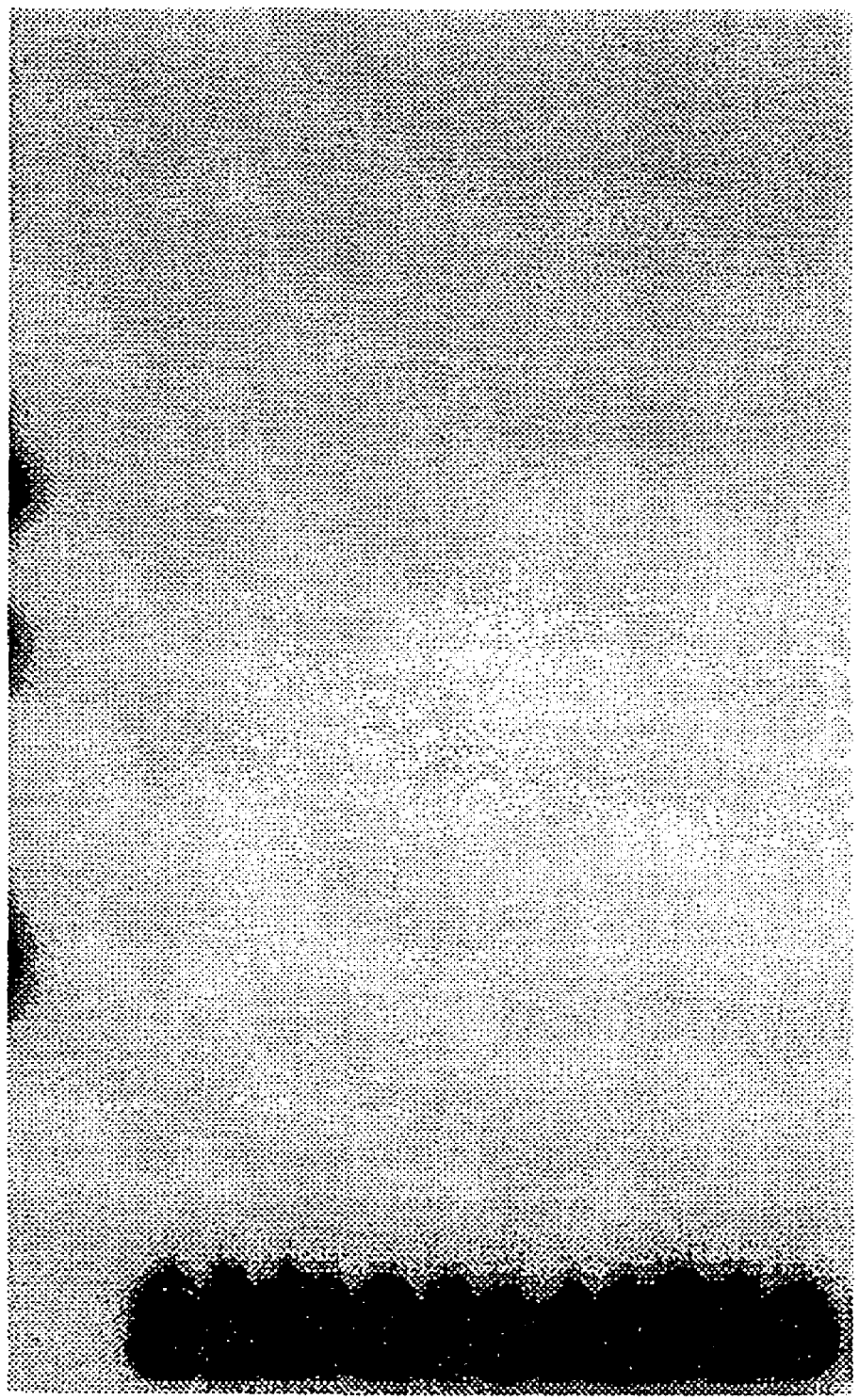
FIG. 2 is an autoradiograph of DEAE cellulose TLC plates illustrating the thermostability of the labeled probe.

The homochromatography analysis provided in FIG. 2 shows an overnight exposure of the plate in which no degradation of the probes was observed. All of the counts were located at the point of origin, showing no release of labeled fragments. Lanes 1–3 are reactions containing probe BW31; Lanes 4–6 include probe BW33; Lanes 7–9 include probe BW35; and Lanes 10–12 are control reactions without template. The results show that the probe is not degraded unless specifically bound to target and is able to withstand the PCR cycling conditions.

In the denaturing gel analysis, 2 µl of each amplification reaction were mixed with 2 µl of formamide loading buffer (described in Example I) and placed on a heat block at 96° C. for 3–5 min. Samples were immediately placed on ice and loaded onto a 6.2% denaturing gradient acrylamide gel, and electrophoresed for 90 minutes at 2000 volts. After electrophoresis, the gel was transferred onto Whatman paper, covered with Saran Wrap, and autoradiographed.

An overnight exposure revealed all of the counts in the 30–40 base pair range, corresponding to the sizes of the probes. Once again, there was no probe degradation apparent, further confirming that probe must be specifically bound to template before any degradation can occur.

EXAMPLE 3

Specificity of Probe Label Release in the Presence of Genomic DNA

In this example, the specificity of probe label release was examined by performing a PCR amplification in the presence of degraded or non-degraded human genomic DNA.

The BW33 kinased probe used in this experiment had a specific activity of $5.28 \times 10^6$ cpm/pmol determined by TCA precipitation following the kinasing reaction. The region amplified was the 350 base pair region of M13mp10w, flanked by primers BW36 and BW42. Primer sequences and locations are listed in Example 1. Human genomic DNA was from cell line HL60 and was used undegraded or degraded by shearing in a french press to an average size of 800 base pairs.

Each 50 µl amplification reaction consisted of $10^{-2}$ or $10^{-3}$ pmol of M13mp10w target sequence, 1 µg of either degraded or non-degraded HL60 genomic DNA added to a mixture containing 50 mM KCl, 10 mM Tris HCl, pH 8.3, 3 mM $MgCl_2$, 10 pmol each of primers BW36 and BW42, 200 µM each of four deoxyribonucleoside triphosphates, 1.25 units Taq DNA polymerase and 10 pmol of isotopically diluted probe BW33.

A master reaction mix was made containing appropriate amounts of reaction buffer, nucleoside triphosphates, primers, probe, and enzyme. Aliquots were made and to them was added M13mp10w template and/or genomic DNA. Control reactions included all reaction components except M13mp10w target DNA or all reaction components except genomic DNA.

Each reaction mixture was overlayed with 50 µl of mineral oil, microcentrifuged, and placed into a thermal cycler. Reaction mixtures were subjected to the following amplification scheme:

| | |
|---|---|
| For 10, 15 or 20 cycles: | 96° C. denaturation, 1 min |
| | 60° C. anneal/extension, 1.5 min |
| Final cycle: | 96° C. denaturation, 1 min |
| | 60° C. anneal/extension, 5.5 min |

After cycling, the mineral oil was extracted using 50 µl of chloroform and samples were stored at 4° C. Samples were subsequently analyzed by a 4% acrylamide gel electrophoresis, and homochromatography analysis.

For the acrylamide gel analysis, 4 µl of each reaction mixture were mixed with 3 µl of 5× gel loading mix, loaded onto a 4% acrylamide gel in 1×TBE buffer, and electrophoresed for 90 minutes at 220 volts. DNA was visualized by UV fluorescence after staining with ethidium bromide.

In the lanes corresponding to control samples containing no M13mp10w target DNA, there were no visible product bands, indicating the absence of any crossover contamination of M13mp10w. All subsequent lanes showed a band at 350 bases corresponding to the expected sequence. The intensity of the band was greater when $10^{-2}$ pmol M13mp10w target DNA was present over $10^{-3}$ pmol in the absence or presence of genomic DNA (degraded or undegraded). The product band intensity increased with increasing number of amplification cycles. Twenty cycles produced a band with twice the intensity of that seen at ten cycles, and fifteen cycles generated a band of intermediate intensity. The amount of PCR product present varied with the amount of starting target template and the number of cycles, and the presence of 1 µg of human genomic DNA, whether degraded or undegraded, showed no effect at all on this product formation.

Figure 3A:
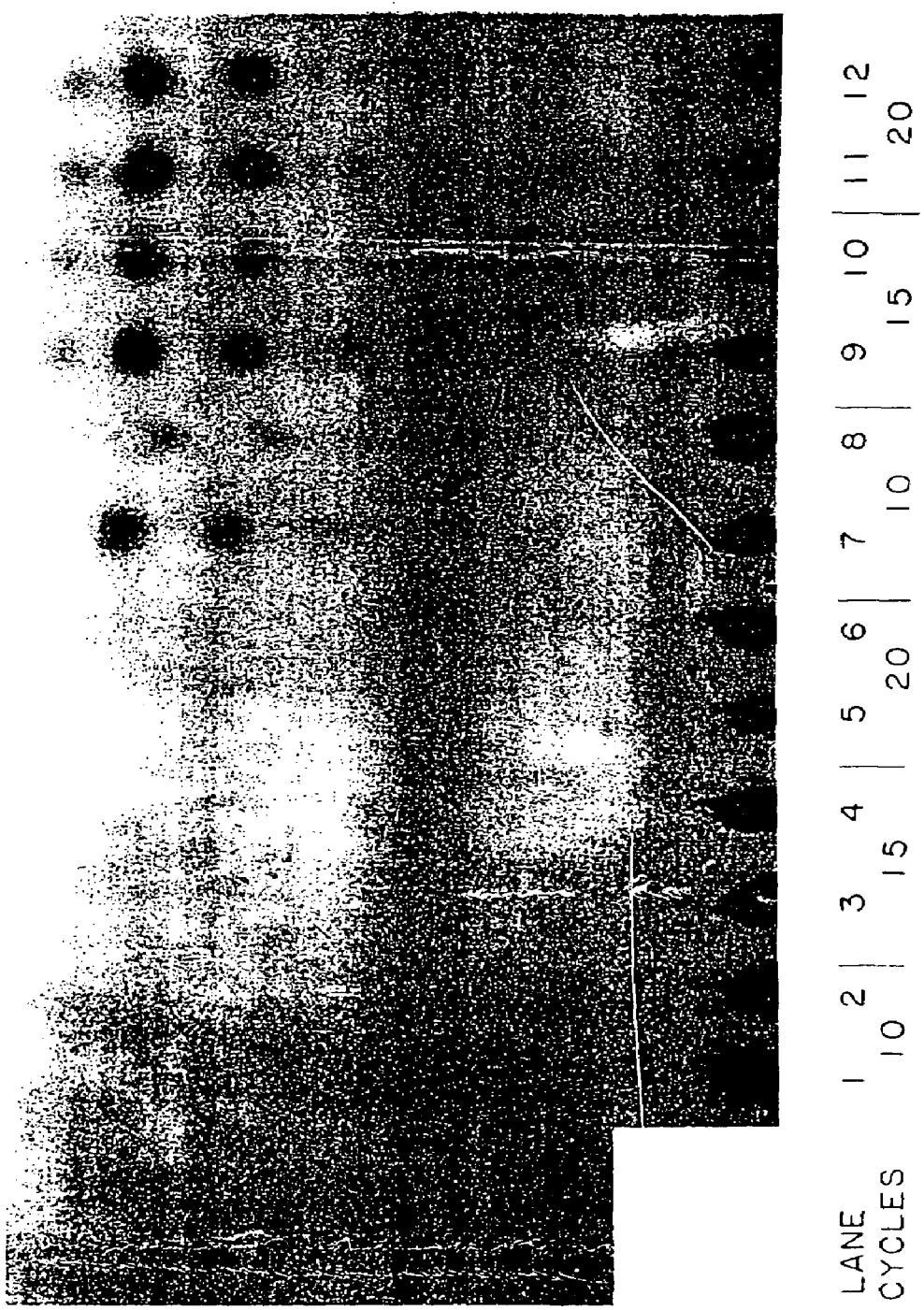
FIGS. 3A and 3B are autoradiographs of DEAE cellulose TLC plates showing that the amount of labeled probe fragment released correlates with an increase in PCR cycle number and starting template DNA concentration.
Figure 3B:
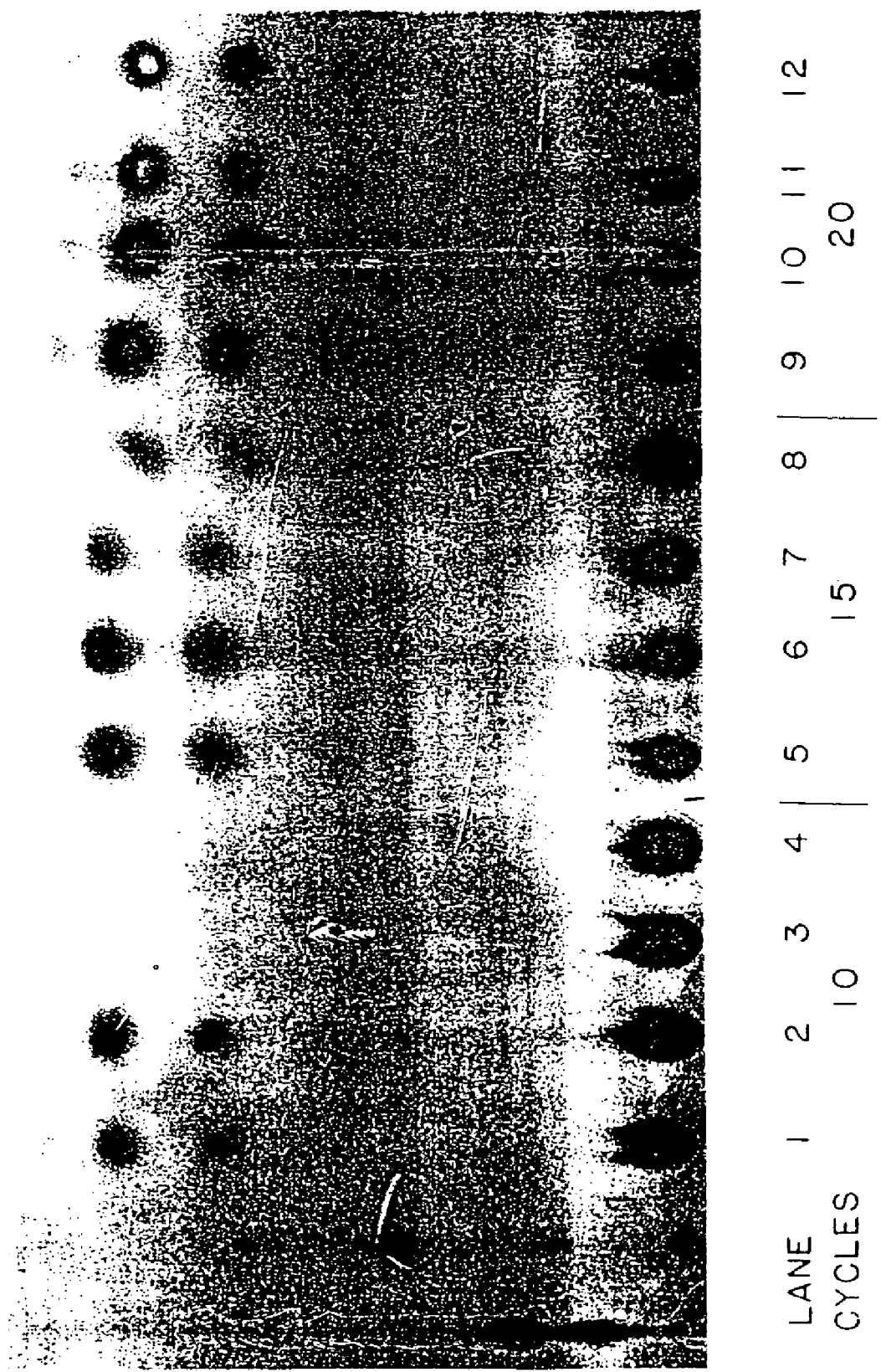

In the homochromatography analysis, 1 µl of each reaction mixture was spotted onto a DEAE thin layer plate, and placed in a developing chamber containing Homo-Mix III at 70° C. After 90 minutes, the plate was removed, allowed to dry, covered with Saran Wrap, and autoradiographed. An overnight exposure is shown in FIG. 3; in FIG. 3A, Lanes 1 to 6 show PCR reaction cycles in the absence of M13mp10w template DNA containing, alternately, degraded and undegraded HL60 DNA at 10, 15, and 20 cycles; and Lanes 7–12 are duplicate loading control reactions containing M13mp10w template DNA without any human genomic DNA at 10, 15 and 20 cycles. In FIG. 3B, reactions are amplified over increasing 5 cycle increments starting at 10 cycles. The M13mp10w template DNA concentration in the reactions shown in Lanes 1, 2, 5, 6, 9, and 10 is $10^{-2}$ pmol, while in lanes 3, 4, 7, 8, 11, and 12 is $10^{-3}$ pmol. The reactions shown in the odd numbered lanes from 1 through 11 contain degraded human genomic DNA, and the even numbered lanes contain non-degraded human genomic DNA. Labeled probe fragments were seen as two well-defined spots migrating at approximately 4 and 5 bases in length on the thin layer plate. As the starting template concentration increased and/or as the cycle number increased, the amount of released labeled probe fragments also increased. The presence or absence of degraded or non-degraded human genomic DNA did not interfere with or enhance probe hybridization and degradation.

The results show that increased amounts of released small probe fragments occur coordinately and simultaneously with specific product accumulation during the course of a PCR assay. The presence or absence of either a large amount of high complexity human genomic DNA or a large number of random DNA "ends" has no effect on specific product accumulation or degree of probe release. Finally, the presence of a large amount of high complexity human genomic DNA does not lead to any detectable probe release in the absence of specific product accumulation.

EXAMPLE 4

PCR with 3' Labeled Probe

A PCR amplification was performed which liberated a hybridized 3' radiolabeled probe into smaller fragments when the probe was annealed to template. The sequences of the probes were as follows:

SEQ ID NO: 8 DG46 = 5' 5541–5512-3'
5'-CGCTGCGCGTAACCACCACACCCGCCGCGC-3'

SEQ ID NO: 9 BW32 = 5' 5541–5512-3'
5'-gatCGCTGCGCGTAACCACCACACCCGCCGCGC-3'

SEQ ID NO: 10 BW34 = 5' 5541–5512-3'
5'-cgtcaccgatCGCTGCGCGTAACCACCA-CACCCGCCGCGC-3'

A. Labeling of Probes with $^{32}$P-cordycepin and Terminal Transferase

Five pmol of each probe (DG46, BW32, and BW34) were individually mixed with 17.4 units of terminal transferase (Stratagene) and 10 pmol of [$\alpha$-$^{32}$P]-cordycepin (cordycepin: 3'-deoxyadenosine-5' triphosphate, New England Nuclear, 5000 Ci/mmol, diluted 3× with ddATP [Pharmacia]) in a 17.5 µl reaction volume containing 100 mM potassium cacodylate, 25 mM Tris-HCl, pH 7.6, 1 mM CoCl$_2$, and 0.2 mM dithiothreitol for 60 minutes at 37° C. The total volume was then phenol/chloroform extracted and ethanol precipitated. Probes were resuspended in 50 µl of TE buffer and run over a Sephadex G-50 spin dialysis column according to the procedure of Sambrook, et al., *Molecular Cloning*, supra. The final concentration of probes was 0.1 pmol/µl. TCA precipitation of the reaction products indicated the following specific activities:

DG46: 2.13×10$^6$ cpm/pmol
BW32: 1.78×10$^6$ cpm/pmol
BW34: 5.02×10$^6$ cpm/pmol Denaturing gradient gel analysis comparison of the 3' radiolabeled probes to 5' kinased probes BW31, BW33 and BW35, show that the 3' radiolabeled probes ran in a similar fashion to the 5' radiolabeled probes.

Once again, the region amplified was the 350 base region on M13mp10w defined by primers BW36 and BW42. Primer sequences and locations are listed in Example 1. Each amplification mixture was prepared adding $10^{-3}$ pmol of the target M13mp10w DNA to a 50 µl reaction volume containing 50 mM KCl, 10 mM Tris HCl, pH 8.3, 3 mM MgCl$_2$, 10 pmol each of primers BW36 and BW42, 200 µM each of four deoxynucleoside triphosphates, 1.25 units of Taq DNA polymerase, and either 2, 10, or 20 pmol of isotopically diluted probe DG46, BW32, or BW34.

A master reaction mix was made containing appropriate amounts of reaction buffer, nucleoside triphosphates, template, and enzyme. Aliquots were made and to them was added the appropriate amount of primers and probes. Control reactions included all reaction components except primers, and all reaction components except probe.

Reaction mixtures were overlaid with 50 µl of mineral oil, microcentrifuged, and placed into a thermal cycler. The amplification scheme was as follows:

| | |
|---|---|
| Fifteen cycles: | 96° C. denaturation, 1 min |
| | 60° C. anneal/extension, 1.5 min |
| Final cycle: | 96° C. denaturation, 1 min |
| | 60° C. anneal/extension, 5.5 min |

After cycling, the mineral oil was extracted using 50 µl of chloroform, and samples were stored at 4° C.

Samples were analyzed by a 4% acrylamide gel, an 8% denaturing gradient acrylamide gel, and by homochromatography. For all three analyses, handling of reaction mixtures was as previously described.

In the 4% acrylamide gel analysis, a sharp band corresponding to the desired product at 350 bases was visible in all of the reaction mixtures except control reactions minus primers. In all of the reaction mixtures containing both primers and probe, a second band was visible at approximately 300 bases. This second band became more intense with increasing probe concentration, and probably corresponded to probe which was either not efficiently 3' radiolabeled or lost the 3' label, allowing probe extension and generating a product.

An overnight exposure of the 8% denaturing gradient acrylamide gel showed a distribution of products ranging from full size probe down to less than 15 bases with all three probes being run. As would be expected, the 5'-3' nuclease activity of Taq DNA polymerase degraded the probe to a point where the degraded probe dissociated from the template.

The wide size distribution of products was illustrative of the continuously changing concentrations of reactants and temperature changes during PCR cycling. Such variations would lead to changes in annealing kinetics of probe and enzyme, allowing for probe to dissociate in a variety of sizes at different times in the cycling routine.

The homochromatography plate revealed the smallest product to be about 10 to 12 bases in length for all the probes examined. Since all three probes had identical sequence except at the 5' tail region, this result shows that for this particular probe sequence at an anneal/extend temperature of 60° C., the probe was degraded to about 10 bases and then dissociated from the template.

EXAMPLE 5

Polymerization Independent 5'-3' Nuclease Activity of Taq DNA Polymerase

Taq DNA polymerase was able to liberate the 5' $^{32}$P-labeled end of a hybridized probe when positioned in proximity to that probe by an upstream primer. A series of primers was designed to lie from zero to twenty bases upstream of hybridized kinased probe BW33. These primers are shown below.

```
BW37  SEQ ID NO: 11  Delta-0  5' 5571-5542 3'
      5'-GCGCTAGGGCGCTGGCAAGTGTAGCGGTCA-3'

BW38  SEQ ID NO: 12  Delta-1  5' 5572-5543 3'
      5'-GGCGCTAGGGCGCTGGCAAGTGTAGCGGTC-3'

BW39  SEQ ID NO: 13  Delta-2  5' 5573-5544 3'
      5'-GGGCGCTAGGGCGCTGGCAAGTGTAGCGGT-3'

BW40  SEQ ID NO: 14  Delta-5  5' 5576-5547 3'
      5'-AGCGGGCGCTAGGGCGCTGGCAAGTGTAGC-3'

BW41  SEQ ID NO: 15  Delta-10 5' 5581-5552 3'
      5'-AAAGGAGCGGGCGCTAGGGCGCTGGCAAGT-3'

BW42  SEQ ID NO: 16  Delta-20 5' 5591-5562 3'
      5'-GAAGAAAGCGAAAGGAGCGGGCGCTAGGGC-3'
```

About 0.5 pmol of probe BW33 and 0.5 pmol of one of each of the primers were annealed to 0.5 pmol M13mp10w in a 10.5 μl reaction volume containing 50 mM KCl, 10 mM Tris-HCl, pH 8.3, and 3 mM MgCl$_2$. Control reaction mixtures contained either 20 μM or 200 μM each of four deoxynucleoside triphosphates. An additional primer, DG47, positioned 530 bases upstream from the probe was used.

```
DG47  SEQ ID NO: 17  Delta-530 5' 6041-6012 3'
      5'-CGGCCAACGCGCGGGGAGAGGCGGTTTGCG-3'
```

Reaction mixtures were heated to 98° C. for 1 min and annealed at 60° C. for 30 min. Tubes were then microcentrifuged and placed in a water bath at 70° C. After ample time for reaction mixtures to equilibrate to temperature, 10, 5, 2.5, 1.25, or 0.3125 units of Taq DNA polymerase were added, and 4 μl aliquots were removed at 2, 5, and 10 minutes. Enzyme was inactivated by adding 4 μl of 10 mM EDTA to each aliquot and placing at 4° C. Reaction mixtures were examined by homochromatography analysis.

Figure 4:
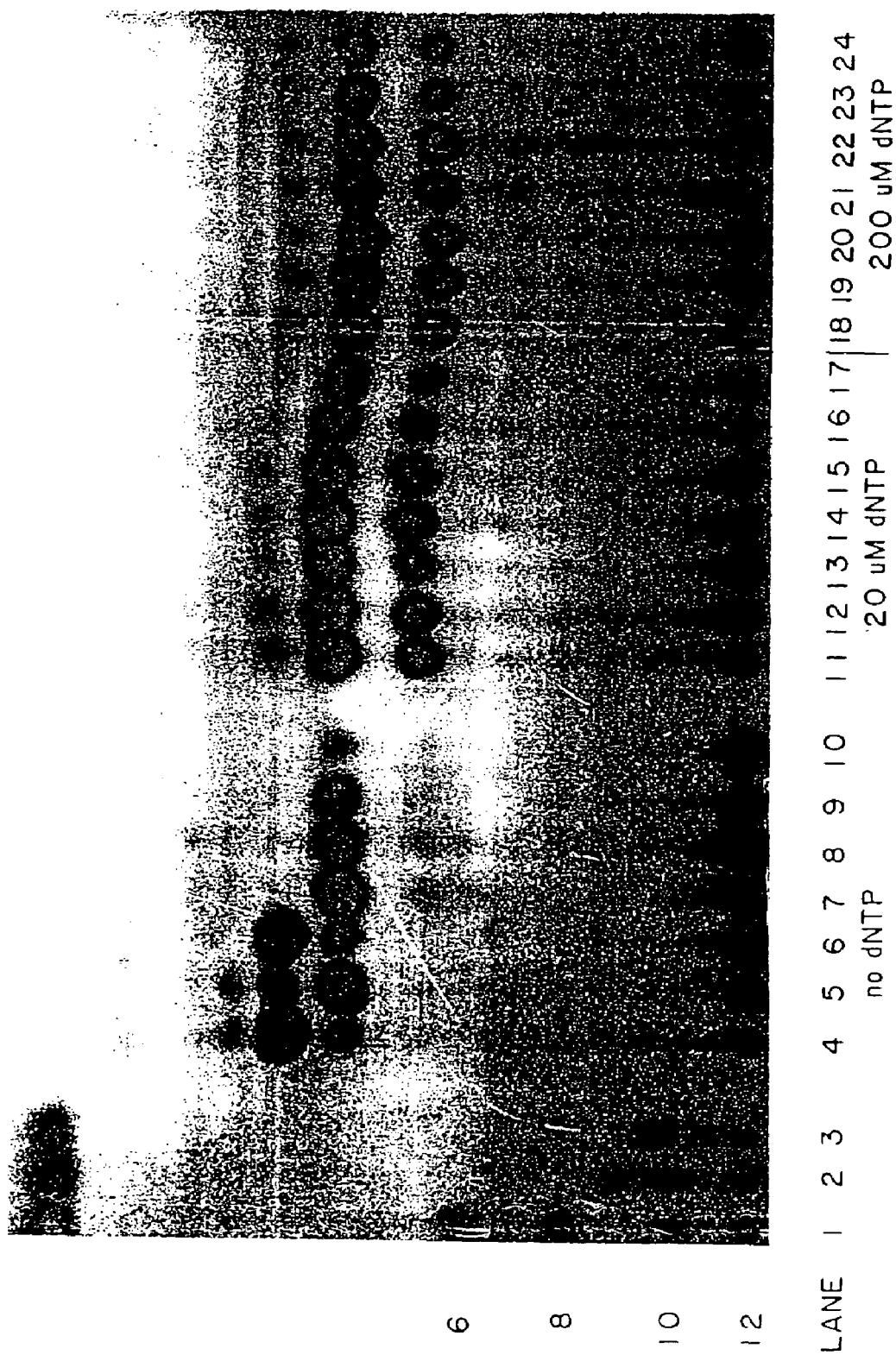
FIG. 4 illustrates the polymerization independent 5'-3' nuclease activity of Taq DNA polymerase shown in the autoradiograph using a series of primers which anneal from zero to 20 nucleotides upstream of the probe.

In the homochromatography analysis, 1 μl of each sample was spotted onto DEAE cellulose thin layer plates and placed into a development chamber containing Homo-Mix III at 70° C. Homo-Mix was allowed to migrate to the top of each plate, at which time the plates were removed, dried, covered with Saran Wrap, and autoradiographed. FIG. 4 shows the results of this experiment.

In FIG. 4, Lanes 1 through 3 contain radiolabeled oligonucleotide molecular size markers of 6, 8, 9, 10, 11, 12, and 13 nucleotides. Lanes 4–10 show reactions for primers BW37, BW38, BW39, BW40, BW41, BW42, and DG47, respectively, in the absence of dNTP's. Lanes 11–24 show control reactions for all primers in the presence of 20 mM or 200 mM dNTP.

In the absence of dNTPs, Taq DNA polymerase generated labeled probe fragments using all of the primers with considerably less label being released as the primer-probe spacing increased. This effect was seen at all the enzyme concentrations examined (0.3125 U to 10 U/reaction) and all timepoints. The sizes of fragments released were the same, about two and three bases in length; however, the primary species varied depending upon which primer was added. The majority species released by the delta zero and delta two primers was one base smaller than that released by the delta one, five, ten, and twenty primers. This nuclease activity was polymerization-independent and proximity-dependent.

In the presence of nucleoside triphosphates, the sizes of labeled probe fragments released, and the relative proportions of each, were identical for all the primers examined. Also, the sizes of products were larger by one to two bases when dNTPs were present. It may be that while the enzyme was polymerizing, it had a "running start" and as it encountered hybridized probe, was simultaneously displacing one to two bases and then cutting, thus generating a larger fragment.

There was no detectable difference in amount of product released when dNTPs were at 20 μM or 200 μM each and no significant differences were seen due to extension times or enzyme concentrations in the presence of dNTPs.

EXAMPLE 6

Example to Illustrate the Nature of Released Product Based on Probe Sequence at the 5' End The effect of strong or weak base pairing at the 5' complementary region of a probe on the size of released product was assessed. Two probes, BW50 and BW51, were designed to contain either a GC- or an AT-rich 5' complementary region. BW50 and BW51 were compared to probe BW33 used in Example V.

```
SEQ ID NO: 18 BW50 = 5' 5521–5496 3'
            5'tatCCCGCCGCGCTTAATGCGCCGCTACA-3'

SEQ ID NO: 19 BW51 = 5' 5511–5481 3'
            5'-gcaTTAATGCGCCGCTACAGGGCGCGTACTATGG
            -3'
``` a,t,g,c=bases which are non-complementary to template strand

BW50, BW51, and BW33 were labeled with $^{32}$P-ATP using polynucleotide kinase and had the following specific activities:

BW50: $1.70 \times 10^6$ cpm/pmol
BW51: $2.22 \times 10^6$ cpm/pmol
BW33: $1.44 \times 10^6$ cpm/pmol The final concentration of all three probes was 0.10 pmol/ul.

Individually, 0.5 pmol of either probe BW50, BW51, or BW33 and 0.5 pmol of primer BW42 were annealed to 0.5 pmol of M13mp10w in a 10.5 μl reaction volume containing 50 mM KCl, 10 mM Tris HCl, pH 8.3, 3 mM $MgCl_2$, and 200 μM each of four deoxynucleoside triphosphates. Control samples contained all reaction components except template. For the annealing step, reaction mixtures were heated to 98° C. for 1 minute and annealed at 60° C. for 30 minutes. Tubes were then microcentrifuged and placed in a water bath at 50° C., 60° C., or 70° C. After ample time for reaction mixtures to equilibrate to temperature, 0.3125 units of Taq DNA polymerase was added. Four μl aliquots were removed at 1, 2, and 5 minutes. Reactions were inactivated by adding 4 μl of 10 mM EDTA to each aliquot and placing at 4° C. Samples were examined by homochromatography analysis and the results are shown in FIGS. 5 and 6.

Figure 5:
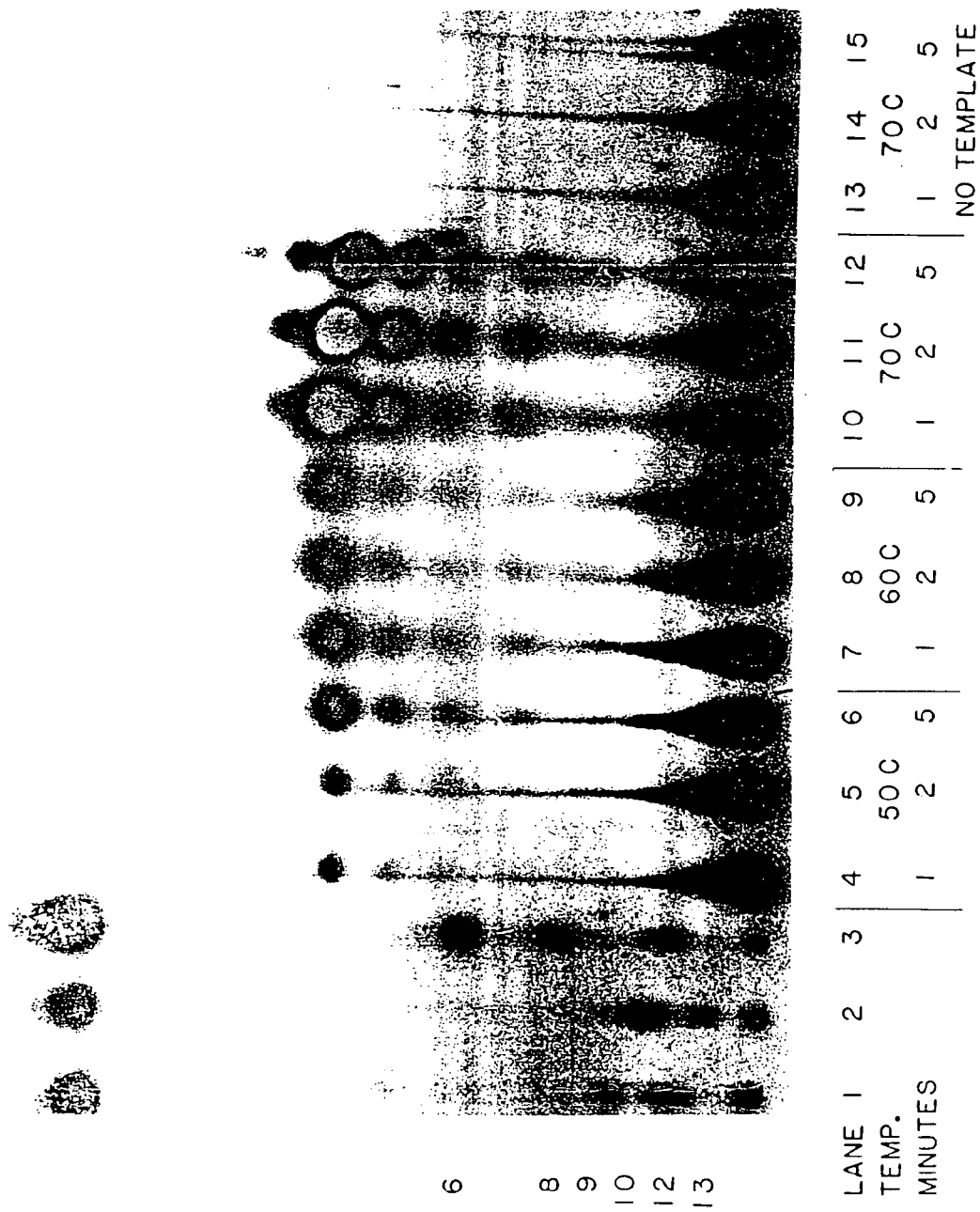
FIG. 5 is an autoradiograph showing the release of labeled probe fragments under increasing incubation temperatures and time, wherein the composition at the 5' end of the probe is GC rich.

FIG. 5 shows the reactions containing the GC-rich probe BW50. Lanes 1–3 contain oligonucleotide molecular size markers of 6, 8, 9, 10, 11, 12, and 13 nucleotides. Lanes 4–6 show extension reactions performed at 50° C. for 1, 2, and 5 minutes. Lanes 7–9 show extension reactions at 60° C. for 1, 2, and 5 minutes. Lanes 10–12 show reactions at 70° C. for 1, 2, and 5 minutes. Lanes 13–15 are control reactions containing all components except template, incubated at 70° C. for 1, 2, and 5 minutes.

Figure 6:
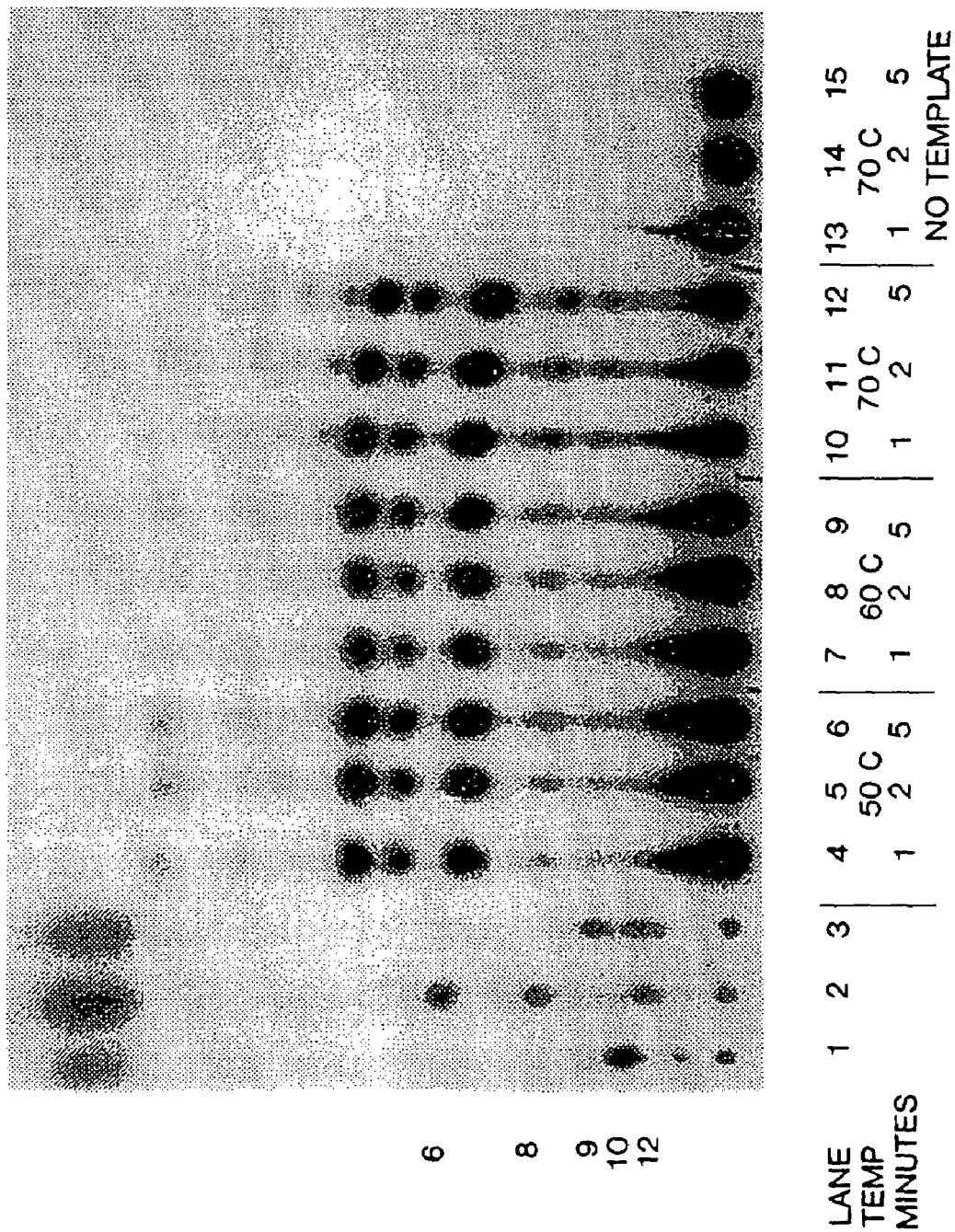
FIG. 6 is an autoradiograph showing the release of labeled probe fragments under increasing incubation temperatures and time, wherein the composition at the 5' end of the probe is AT rich.

FIG. 6 shows the reactions containing the AT rich probe BW51. As in FIG. 5, Lanes 1–3 are oligonucleotide molecular size markers of 6, 8, 9, 10, 11, 12, and 13 nucleotides. Lanes 4–6 are extension reactions performed at 50° C. for 1, 2 and 5 minutes. Lanes 7–9 are reactions at 60° C. at 1, 2, and 5 minutes. Lanes 10–12 are reactions at 70° C. at 1, 2, and 5 minutes. Lanes 13–15 are control reactions containing all components except template, incubated at 70° C. for 1, 2, and 5 minutes.

The results demonstrate that the nature of probe label release was dependent on temperature and base composition at the 5' end. The more stable GC-rich probe BW50 showed little label release at 50° C. (FIG. 5, Lanes 4–6) and increasingly more at 60° C. (FIG. 5, Lanes 7–9) and 70° C. (FIG. 5, Lanes 10–12). The major products released were about 3–5 bases in length. BW51, which was AT-rich at the 5' end, showed as much label release at 50° C. (FIG. 6, Lanes 4–6) as was observed at the higher temperatures. In addition, the AT-rich probe generated larger-sized products than the GC-rich probe. The base composition of the AT-rich probe may give the opportunity for a greater "breathing" capacity, and thus allow for more probe displacement before cutting, and at lower temperatures than the GC-rich probe.

EXAMPLE 7

HIV Capture Assay

The following is an example of the use of a dual labeled probe containing biotin in a PCR to detect the presence of a target sequence. Two oligonucleotides, BW73 and BW74, each complementary to a portion of the HIV genome, were synthesized with a biotin molecule attached at the 3' end of the oligonucleotide. The 5' end of each oligonucleotide was additionally labeled with $^{32}$P using polynucleotide kinase and gamma-$^{32}$P-ATP. The two oligonucleotides PH7 and PH8 are also complimentary to the HIV genome, flank the region containing homology to the two probe oligonucleotides, and can serve as PCR primers defining a 142 base product. The sequences of these oligonucleotides are shown below.

```
SEQ ID NO: 20 BW73 = ³²P-GAGACCATCAATGAGGAAGCTGCAG
                    AATGGGAT-Y

SEQ ID NO: 21 BW74 = ³²P-gtgGAGACCATCAATGAGGAAGCTG
                    CAGAATGGGAT-Y

SEQ ID NO: 22 PH7  = AGTGGGGGGACATCAAGCAGCCATGCAAAT

SEQ ID NO: 23 PH8  = TGCTATGTCAGTTCCCCTTGGTTCTCT
```

In the sequences, "Y" is a biotin, and lower case letters indicate bases that are non-complementary to the template strand.

A set of 50 μl polymerase chain reactions was constructed containing either BW73 or BW74, each doubly labeled, as probe oligonucleotides at 2 nM. Additionally, HIV template in the form of a plasmid clone was added at either $10^2$ or $10^3$ copies per reaction, and primer oligonucleotides PH7 and PH8 were added at 0.4 μM each. Taq polymerase was added at 1.25 U per reaction and dNTPs at 200 μM each. Each reaction was overlayed with 50 μl of oil, spun briefly in a microcentrifuge to collect all liquids to the bottom of the tube, and thermocycled between 95° C. and 60° C., pausing for 60 seconds at each temperature, for 30, 35, or 40 cycles. At the conclusion of the thermocycling, each reaction was extracted with 50 μl of $CHCl_3$ and the aqueous phase collected.

Each reaction was analyzed for amplification by loading 3 μl onto a 5% acrylamide electrophoresis gel and examined for the expected 142 base pair product. Additionally, 1 μl of each reaction was examined by TLC homochromotography on DEAE cellulose plates. Finally, each reaction was further analyzed by contacting the remaining volume with 25 μl of a 10 mg/ml suspension of DYNABEADS M-280 streptavidin labeled, superparamagnetic, polystyrene beads. After reacting with the beads, the mixture was separated by filtration through a Costar Spin X centrifuge filter, the filtrate collected and the presence of released radiolabel determined.

FIG. 7 contains images of the two gels used and shows that 142 base pair product occurs in all reactions, with and without probe, and increases in amount both as starting template was increased from $10^2$ to $10^3$ copies and as thermocycling was continued from 30 to 35 and 40 cycles.

FIG. 8 is a composite of two autoradiographs of the TLC analysis of aliquots of the PCRs and show that radiolabel release occurs and increases in amount with both increase in starting template and with longer thermocycling. In the first TLC of PCRs using BW73, lanes 1 and 3 contain radiolabeled oligonucleotides 2 and 3 bases in length as size standards. Lanes 4, 5, and 6 contain samples from PCRs with $10^2$ starting copies of template and lanes 7, 8, and 9 with $10^3$ starting copies. Samples in lanes 4 and 7 were thermocycled for 30 cycles; in lanes 5 and 8 for 35 cycles; and in lanes 6 and 9 for 40 cycles. In the second TLC of PCRs using BW74, lanes 1 and 2 are the radiolabeled 2 mer and 3 mer, lanes 4, 5, and 6 contain samples from PCRs with $10^2$ starting copies of template thermocycled for 30, 35, and 40 cycles, respectively, and lanes 7, 8 and 9 with $10^3$ copies of starting template thermocycled for 30, 35 and 40 cycles, respectively. The size of the released label is smaller with BW73, which has no 5' non-complementary bases, and larger with BW74, which has a 5' three base non-complementary extension.

Each chromatogram was additionally analyzed by two-dimensional radioisotope imaging using an Ambis counter. The results of Ambis counting and bead capture counting are shown in Table 1 The good agreement in the two methods of measuring label release demonstrates the practicality of the use of labeled biotinylated probes and avidinylated beads in PCRs to determine product formation.

TABLE 1

|  | Number of Cycles | % of Label Released | |
|---|---|---|---|
|  |  | Ambis | Capture |
| BW73 | 30 | 6.9 | 10.8 |
| $10^2$ copies | 35 | 29.0 | 32.7 |
|  | 40 | 47.2 | 47.2 |
| $10^3$ copies | 30 | 11.8 | 16.8 |
|  | 35 | 35.6 | 39.3 |
|  | 40 | 53.4 | 52.5 |
| BW74 | 30 | 8.3 | 7.9 |
| $10^2$ copies | 35 | 20.7 | 25.2 |
|  | 40 | 43.2 | 48.3 |
| $10^3$ copies | 30 | 15.7 | 14.7 |
|  | 35 | 32 | 37.7 |
|  | 40 | 46 | 47.9 |

EXAMPLE 8

Probe Labeling and Solid Phase Extractant Methodology

In one embodiment of the present invention, a separation step is employed after probe cleavage but prior to determination of the amount of cleaved probe to separate cleaved probe products from uncleaved probe. Two alternate separation methods are preferred: (1) the use of avidinylated or streptavidinylated magnetic particles to bind probes labeled at the 3'-end with biotin and at the 5'-end with a fluorophore; the magnetic particles bind both uncleaved probe and the 3'-fragment that is the product of probe cleavage; and (2) the use of magnetic ion exchange particles that bind oligonucleotides but not mono- or dinucleotides that are typically labeled at the 5'-end with a fluorophore or $^{32}P$. Various aspects of these alternate strategies are discussed below.

A. Avidinylated Magnetic Particles

The separation system involving 3'-biotinylated probes and magnetic avidinylated (or streptavidinylated) beads is carried out preferably with beads such as Dynabeads™ from Dynal; these beads have a biotin binding capacity of approximately 100 pmoles per 50 µl of beads. Nonspecific adsorption is minimized by first treating the beads with both Denhardt's solution and carrier DNA.

The probe for streptavidin-biotin separation methods requires a biotin moiety at the 3'-terminus and a fluorophore at the 5'-terminus. The 3'-biotin functions both as a ligand for separation by streptavidinylated (or avidinylated) beads and as a block to prevent the extension of probe during the amplification. Post-synthesis modifications can be simplified by extending each end of the probe with a different nucleophile; for instance, one can add an amine to the 3'-end for the addition of biotin and a blocked thiol at the 5'-end for later addition of the fluorophore. The 3'-biotinylated probes can be prepared in a variety of ways; some of which are illustrated below.

An NHS-active ester derivative of biotin can be added to the 3'-amine of the probe by the reaction mechanism shown in FIG. 9. The resulting linkage creates a secondary hydroxyl gamma to the amide carbon 1, which may result in instability during the repeated thermal cycling of a typical PCR. For instance, thermal cycling for 40 cycles can render as much as 6% of the initial probe added unable to bind to magnetic avidinylated particles. When the bond between the probe and the attached biotin breaks down as a result of thermal cycling, the probe can no longer be separated from the cleaved products and contributes to the background. Although one can help overcome this problem by attaching more than one biotin to the probe, several alternate methods for attaching biotin to an oligonucleotide may yield more stable products.

One can react biotin hydrazide with aldehydes generated from a 3'-ribose on the probe to yield a biotinylated oligonucleotide. For this strategy, the 3'-nucleotide of the probe contains a ribose sugar in place of the deoxyribose sugar. During synthesis, the 3'-ribose is attached to the solid support by either its 2'- or 3'-OH. Following synthesis, the completed oligonucleotide is released from the solid support, and the vicinal diols of the ribose are oxidized by sodium periodate ($NaIO_4$) to aldehydes that are then reacted with the biotin hydrazide, as shown in FIG. 10, and the product is reduced by sodium borohydride ($NaBH_4$). However, the resulting biotinylated probe does not bind efficiently to avidinylated magnetic particles. The use of biotin long chain hydrazide, a compound also shown in FIG. 10, can solve this problem.

One can attach the biotin to the probe during probe synthesis using a soluble biotin phosphoramidite, as shown in FIG. 11. The synthesis begins with a base attached to controlled porous glass (CPG), which is ultimately discarded. A phosphoramidite, which allows the generation of a 3'-phosphate on ammonium hydroxide deprotection of the synthetic oligonucleotide, is added. The biotin phosphoramidite is then added, and the oligonucleotide synthesized is as shown in FIG. 11, which also shows the final product. This method of attachment allows the use of 5'-amine terminated oligonucleotides for the attachment of a fluorophore. The use of a 3'-amine for the attachment of biotin limits the chemistry of attachment of fluorophore to 5'-thiols. Utilization of a biotin phosphoramidite in which one of the biotin nitrogens is blocked may improve the synthesis of the biotin labeled probe.

One can also use a commercial reagent that consists of biotin directly attached to porous glass; the reagent is the starting substrate for probe synthesis and is shown in FIG. 12. This method of attachment allows the use of 5'-amine terminated oligonucleotides for the attachment of a fluorophore. The use of a 3'-amine for the attachment of biotin limits the chemistry of attachment of fluorophore to 5'-thiols. Enzymatic methods of attachment of modified nucleotides to the 5'-ends of oligonucleotides are also available, although limited in their generality and practicality.

B. Magnetic Ion Exchange Matrices

One can use commercially available polyethyleneimine (PEI) matrices (cellulose-, silica-, and polyol polymer-based) particles to separate cleaved from uncleaved probe. For instance, Hydrophase PEI, Selectacel™ PEI, Bakerbond™ PEI, and Amicon PAE 300, 1000, and 1000L are all commercially available PEI matrices that give separation of uncleaved probe from cleaved probe products.

Commercially available activated cellulose magnetic particles, such as Cortex MagaCell™ particles can be derivatized with PEIs of various lengths, such as PEI600, PEI1800, and PEI10,000, and at different molar ratios of PEI per gram of matrix. However, all sizes of oligonucleotides and coumarin-labeled oligonucleotides bind to magnetic cellulose and agarose beads whether or not they have been derivatized with PEI (the specificity seen with oligonucleotides on commercially available PEI matrices is lost when one labels the oligonucleotides with coumarin). The addition of high concentrations of salt (2.0 M NaCl) or N-methyl pyrrolidone (10 to 20%) partially increases the specificity, and other cosolvents such as SDS, Brij 35, guanidine, and urea can also be used to increase the specificity of binding. However, 8 M urea provides efficient blocking of the nonspecific binding of coumarin labeled di- and tri-nucleotides to both Bakerbond™ PEI and magnetic Cortex™ PEI derivatized particles, although the use of N-substituted ureas may be more preferred.

As noted above, Cortex Biochem sells a variety of activated cellulose coated magnetic particles that can be linked to PEI. The most convenient of these is the periodate activated matrix. The protocol recommended by the manufacturer to attach amines to the periodate activated matrix, however, has several problems: the reaction of an amine with an aldehyde results in imines that are labile and can be hydrolyzed or reacted further with amines; during the step to block remaining aldehydes by the addition of excess ethanolamine, the PEI can be displaced by ethanolamine, thus removing the PEI from the matrix; during the conjugation reaction under basic conditions, aldol condensation can lead to reaction among the aldehyde groups, thereby resulting in aggregation of the particles; and reaction of aldehydes under basic conditions may result in free radicals that can attack the cellulose, and participate in a variety of reactions.

To stabilize the imine, a reduction step (with $NaBH_4$ and $NaBH_3CN$) can be included; however, this step can result in the production of gas, a decrease in the mass of the particles, and particle agglutination. These unwanted effects may result from the production of free radicals. The complications resulting from conjugation to active aldehydes may be avoided through the use of epoxide chemistry. The resulting beta-hydroxyamines are stable and do not require reduction. In addition, because oxygen may participate in the generation of free radicals, the removal of oxygen from the system should minimize free radical formation, especially during the reduction step. In one synthesis of PEI derivatized cellulose coated magnetic particles, the ethanolamine blocking step was eliminated and the preparation purged overnight with helium prior to and during reduction with sodium cyanoborohydride. There was little aggregation in the final preparation.

Polyacrolein magnetic particles can be derivatized with both PEI600 and ethylene diamine, and the non-specific binding of coumarin labeled di- and trinucleotides can be inhibited by high concentrations of NMP. The use of longer chained PEI polymers may mask nonspecific backbone interaction with small, coumarin labeled oligonucleotides.

One important factor in selecting a magnetic matrix for use in the present method is the amount of background fluorescence contributed by the matrix. One strategy to minimize this background fluorescence is to select fluorophores with excitation and emission maxima that minimally overlap the background fluorescence spectra of the buffer, matrix, and clinical samples. In addition, the fluorescent background may result from the presence of contaminants in the matrix that might be removed by extensive pretreatment prior to binding.

C. Chemistry of Attachment of the Fluorophore to the Probe

As noted above, the preferred label for the probe, regardless of separation strategy, is a fluorophore. There appears to be interaction between the oligonucleotide probe and the attached fluorophore. This interaction may be responsible for the reported quenching observed when fluorophores have been attached to oligonucleotides. One should select fluorophores that minimally interact with DNA when attached to the 5'-terminus of a nucleic acid.

Three preferred fluorophores are 7-diethylamino-3-(4'-maleimidylphenyl)-4-methyl coumarin (CPM), 6-(bromomethyl)fluorescein (BMF), Lucifer Yellow iodoacetamide (LYIA), and 5-(and 6-)carboxy-X-rhodamine succinimidyl ester, with CPM preferred due to several properties: large extinction coefficient, large quantum yield, low bleaching, and large Stokes shift. The fluorophore can be attached through a thiol attached to the 5'-phosphate group of the probe, but in the case of CPM, this process yields an aryl maleimide, which can be unstable under thermocycling conditions.

A number of commercial instruments are available for analysis of fluorescently labeled materials. For instance, the ABI Gene Analyzer can be used to analyze attomole quantities of DNA tagged with fluorophores such as ROX (6-carboxy-X-rhodamine), rhodamine-NHS, TAMRA (5/6-carboxytetramethyl rhodamine NHS), and FAM (5'-carboxyfluorescein NHS). These compounds are attached to the probe by an amide bond through a 5'-alkylamine on the probe. Other useful fluorophores include CNHS (7-amino-4-methyl-coumarin-3-acetic acid, succinimidyl ester), which can also be attached through an amide bond.

Modifications may be necessary in the labeling process to achieve efficient attachment of a given fluorophore to a particular oligonucleotide probe. For instance, the initial reaction between a 5'-amine terminated probe and 7-diethylaminocoumarin-3-carboxylate NHS ester was very inefficient. The probe, which had been phosphorylated at the 3'-end to prevent extension of the probe during amplification, had significant secondary structure, one conformation of which placed the 5'-amine and the 3'-phosphate in close enough proximity to form a salt bridge. This structure may have prevented the 5'-amine from being available for reacting with the NHS ester, thus causing the low yield of product. Addition of 25% N-methylpyrrolidinone (NMP) markedly improved the efficiency of the reaction.

One can also use both a fluorophore and quenching agent to label the probe. When the probe is intact, the fluorescence of the fluorophore is quenched by the quencher. During the present method, the probe is cleaved between the fluorophore and the quencher, allowing full expression of the fluorophore fluorescence. Quenching involves transfer of energy between the fluorophore and the quencher, the emission spectrum of the fluorophore and the absorption spectrum of the quencher must overlap. A preferred combination for this aspect of the invention is the fluorophore rhodamine 590 and the quencher crystal violet.

One such probe is shown in FIG. 13. The synthesis of this construct requires attachment of a rhodamine derivative through a 5'-thiol and the attachment of the crystal violet through an amine extending from a thymidine two bases away. The separation of the two moieties by two phosphodiester bonds increases the chances for cleavage by the DNA polymerase between them.

Initial attempts to attach the crystal violet by reaction between a lactone and amine were unsuccessful. The crystal violet was modified to generate an active acyl azide, shown in FIG. 14. This form of crystal violet was reacted with amine-modified DNA, and the desired product was purified on reverse phase HPLC.

Attempts to react the rhodamine-X-maleimide group with the 5'-thiol were unsuccessful. This was also the case when the rhodamine-X-maleimide was reacted prior to addition of the crystal violet. This may be because the deblocked 5'-thiol reacts with the acrylamide double bond in the thymidine spacer arm (see FIG. 13). An alternate method for the addition of an amine to the thymidine is shown in FIG. 15.

This example provides general guidance for attaching a biotin to the 3'-end of an oligonucleotide probe and a fluorophore to the 5'-end of an oligonucleotide probe. Those of skill in the art will recognize that a number of methods for such attachments are known in the art and that the present invention is not limited by the particular method chosen to label the probe.

EXAMPLE 9

Protocol for AmpliWax™ Mediated PCR with UNG and dUTP

The PCR process can be improved with respect to specificity of amplification by processes and reagents described more fully in PCT patent application Serial No. 91/01039, filed Feb. 15, 1991; U.S. patent application Ser. No. 481,501, filed Feb. 16, 1991; PCT patent application Serial No. PCT/US 91/05210, filed Jul. 23, 1991; U.S. patent application Ser. No. 609,157, filed Nov. 2, 1990; and U.S. patent application Ser. No. 557,517, filed Jul. 24, 1990. The disclosures of these patent applications are incorporated herein by reference, and the following protocol demonstrates how these improved PCR methods can be used in conjunction with the present method for superior results. All reagents can be purchased from Perkin-Elmer Cetus Instruments (PECI, Norwalk, Conn.).

This protocol essentially involves three components: MicroAmp™ tubes containing dNTPs, primers, magnesium, and Tris that have been covered with wax; Premix B to which is added AmpliTaq® DNA Polymerase and UNG (and is therefore called the Enzyme Mixture); and Premix C to which are added the test sample and probe. The Enzyme Mixture and test sample with probe are made and added above the wax layer. The tubes are then placed in a TC9600 thermocycler and thermocycled. The protocol below assumes a 50 µl reaction, with test samples of no more than 27 µl, and the target is HIV.

The reagents are preferably supplied as follows. MicroAmp™ tubes containing 12.5 µl of Premix A and one 12 mg AmpliWax™ PCR pellet per tube are prepared. Premix A contains 1 µM SK 145 primer and 1 µM SK431 primer (neither primer is biotinylated), 800 µM dATP, 800 µM dGTP, 800 µM dCTP, 800 µM dUTP, 15 mM $MgCl_2$, and 10 mM Tris-HCl, pH 8.3. The AmpliWax™ pellet consists of a 55° C.-melting paraffin (Aldrich Chemical Co.) containing 0.15% Tween 65, and the wax pellet and Premix A bottom layer are added together in a DNA-free room. The wax pellet is then melted to form a vapor barrier on top. This barrier will retain its integrity when the tubes are stored at 4 to 25° C., and the PCR reagents below the barrier are storage stable for months at 4° C. There is no mixing of material added above the barrier until the wax is melted during the initial stages of thermal cycling. Control tubes are identical but contain no primer.

Premix B buffer contains 10 mM Tris-HCl, pH 8.3, and 50 mM KCl and is used for dilution of the enzymes AmpliTaq® DNA polymerase and UNG. About 2.6 µl of Premix B buffer are used per reaction.

Premix C buffer is prepared as a 10× concentrate, which contains 105 mM Tris-HCl, pH 8.3, and 715 mM KCl and is added to the test DNA sample so that the final Tris and KCl concentrations in the final reaction are 10 mM and 50 mM, respectively. The probe is also added in this layer, as well as carrier DNA, if any. If plasmid controls are run, about 1 µg of human placental DNA (1 µg/µl in 10 mM Tris, pH 8, 1 mM EDTA, and 10 mM NaCl, which has been sheared, phenol/chloroform extracted, chloroform extracted, and ethanol precipitated) per reaction is usually added as carrier DNA. About 3.3 µl of the 10× stock of Premix C are added per reaction.

The probe is prepared as a 5 µM stock and designated as LG101C. Probe LG101C has a 3'-phosphate to prevent extension of the probe and a 7-diethylaminocoumarin-3-carboxylate attached to a 5'-amino aliphatic group on the oligonucleotide by an amide bond. The nucleotide sequence of the probe is shown below:

SEQ ID NO: 24 LG101C: 5'-GAGACCATCAATGAG-GAAGCTGCAGAATGGGAT

This probe should be stored at −20° C. in the dark.

AmpliTaq® DNA polymerase is provided at a stock concentration of 5 U/µl from PECI, and UNG is provided at a stock concentration of 1 U/µl from the same vendor. One can also run plasmid calibration samples, and for this purpose, the preparation of stock dilutions (copies/ml) of 300, 1,000; 3,000; 10,000; 30,000; 100,000; and 1,000,000 with GeneAmplimer™ Positive Control DNA is helpful. This DNA consists of the HIVZ6 genome rearranged to interrupt the pol region, and so block infectivity, inserted into plasmid pBR322.

Each final reaction will consist of 12.5 µl of Premix A; 2.6 µl of Premix B; 3.3 µl of Premix C; 2 µl of LG101C probe; 27 µl of test sample; 0.4 µl of AmpliTaq® DNA polymerase; and 2 µl of UNG yielding a final volume of 49.8 µl. This mixture comprises 250 nM of each primer, 200 µM of each dNTP; 3.75 mM $MgCl_2$; 50 mm KCl, 10 mM Tris-HCl, pH 8.3; 200 nM of probe; 2 units of UNG; and 2 units of polymerase.

To run the reaction, one first prepares the Enzyme Mixture in a DNA-free hood or room by mixing, per reaction, 2.6 µl of Premix B buffer, 0.4 µl of AmpliTaq® DNA polymerase, and 2 µl of UNG. For every 16 reactions that will be run, one should prepare enough Enzyme Mixture for 18 reactions to ensure enough material. The Enzyme Mixture is then added to each MicroAmp™ tube containing wax-covered Premix A over the wax in a DNA-free hood or room. A single sampler tip can suffice for all transfers, and 5 µl of Enzyme Mixture are added to each tube.

In the sample preparation area, the Sample Mixture is prepared by mixing, per reaction, 3.3 µl of 10× Premix C Buffer, 27 µl of sample (for quantification controls, add 10 µl of stock dilution and 17 µl of water), and 2 µl of probe (carrier DNA, if any, is mixed with sample). Then, using a separate sampler tip for each transfer, add 32.3 µl of Sample Mixture to each tube; the volume imbalance between the Enzyme Mixture and Sample Mixture assures complete mixing. One should also set up two control tubes lacking primers to serve as a measure of probe cleavage resulting from thermal cycling. This control typically contains 1,000 copies of control template. In addition, one should set up a dilution series of plasmid to calibrate the assay. This calibration is typically in the range of 3 to 10,000 copies of HIV target per sample. After the above steps are completed, the tubes are capped and assembled into the TC9600 tray.

The thermal cycler profile is as follows: 1 cycle of 50° C. for 2 minutes; 5 cycles of 95° C. for 10 seconds, 55° C. for 10 seconds, and 72° C. for 10 seconds; and 35 cycles of 90° C. for 10 seconds, 60° C. for 10 seconds, and 72° C. for 10 seconds. When thermal cycling is complete, the tubes are removed from the TC9600 and stored at −20° C., if necessary. Prolonged soaking of the tubes at above 70° C. is not recommended, and alkaline denaturation should not be employed.

A number of controls are useful, including a no-template control to determine contamination of reaction mixtures as well as amplification of nonspecific products that may result in probe cleavage and give nonspecific signals; a no-primer control to prove a measure of nonamplification related cleaveage of the probe that might contribute to background (one might also include some clinical samples in the tests to detect the presence of components that may result in probe cleavage); and quantitation controls.

To remove PCR product from beneath the wax layer that will form after amplification using the above protocol, one can withdraw sample after poking a sampler tip through the center of the wax layer, advancing the tip slowly with gentle pressure to minimize the chance that reaction mixture will spurt past the tip and contaminate the lab. Steadying the sampler with one finger of the hand holding the reaction tube greatly increases control. Slim (gel-loading) sampler tips penetrate the wax especially well. A slicing motion rather than a poking motion also facilitates penetration and helps to assure that the tip will not be clogged with wax. If the tip picks up a piece of wax, the wax can normally be dislodged by gentle rubbing against the remaining wax.

One can also freeze the reaction tubes (e.g., in dry ice ethanol or overnight in a freezer), thaw them, and spin briefly in a microfuge (angle rotor). The wax layer will be heavily fractured, allowing sampler insertion without any chance of clogging. Wax fragments can be wiped from the sampler tip against the inner wall of the tube. This method is especially convenient for positive displacement samplers, which often have tips so thick that direct penetration of the intact wax layer is hard. Either of the above methods should exclude wax from the withdrawn sample so completely that chloroform extraction is unnecessary.

Although the foregoing invention has been described in some detail for the purpose of illustration, it will be obvious that changes and modifications may be practiced within the scope of the appended claims by those of ordinary skill in the art.

EXAMPLE 10

Solid Phase Extraction with Bakerbond™ PEI

This example provides a protocol for sampling a PCR mixture in which the amplification was carried out in the presence of a fluorescently labeled (a coumarin derivative) probe according to the method of the present invention.

The preparation of certain stock reagents facilitates practice of this protocol. One such reagent is Eppendorf tubes containing 50 mg of pre-washed Bakerbond PEI matrix. The Bakerbond™ PEI can be obtained from J.T. Baker (product No. 7264-00) and is a silica based, 40 µm particle size, 275 angstrom pore size. The matrix is prepared by washing First with water, then ethanol; then water; and then a mixture of 10 mM Tris, pH 8.3, 50 mM KCl, 1 mM EDTA, 2 M NaCl, and 8 M urea; and then equilibrated in 10 mM Tris, pH 8.3, 50 mM KCl, 1 mM EDTA, 500 mM NaCl, and 8 M urea. Following distribution, 15 µl of water is added to each tube to keep the matrix hydrated. The tubes should be stored at 4° C.

Binding buffer can also be prepared as a stock solution, and the composition is 10 mM Tris, pH 8, 500 mM NaCl, 50 mM KCl, 1 mM EDTA, and 8 M urea. The binding buffer should be stored at 4° C., although urea may precipitate at this temperature. The binding buffer can be warmed briefly before use to resuspend the urea.

Certain equipment is useful in carrying out this protocol. During the binding step, the tubes should be mixed to keep the matrix in suspension, and a Vortex Genie 2 mixer (available from Fischer Scientific, Cat. No. 12-812, with the 60 microtube holder, Cat. No. 12-812-B) is useful for this purpose. In addition, an Eppendorf microfuge, an Hitachi Model 2000 spectrofluorometer, and microfluorimeter quartz cuvettes with 2 mm internal width and a 2.5 mm base path length (available from Starna Cells, Inc., No. 18F Q 10 mm 5) are also useful in carrying out this protocol.

Appropriate controls should also be performed, and the binding step requires three controls. The control for background fluorescence involves the preparation of a sample that contains all components of the PCR amplification except probe. The control sample should be processed identically as the actual test samples in that 20 µl will be added to matrix and the fluorescence present in the supernatant measured. This control provides a way to measure background fluorescence present in the matrix, binding buffer, and any of the components in the PCR amplification mixture and also provides a measurement of the amount of fluorescence present in clinical samples.

The second control provides a measurement for inadvertent probe breakdown and for the binding reaction and consists of a mock PCR amplification mixture that contains all of the components including probe but is not subjected to thermal cycling. The control sample should be processed identically as the actual test samples in that 20 µl will be added to matrix and the fluorescence present in the supernatant measured. This control provides a way to measure the presence of probe breakdown on storage as well as the efficiency of the binding reaction. If no breakdown occurred and if the binding reaction is complete, the fluorescence of the supernatant following binding to the Bakerbond™ PEI should be similar to the background measured in the first control.

The third control provides a way to measure the input amount of probe. The sample prepared for the second control can be used for this measurement. However, in this case, 20 µl are added to a tube containing 290 µl of binding buffer without matrix. This control can be used to determine the input amount of probe.

To begin the protocol, one first determines the number of binding tubes required; this number is the sum of test samples and controls. The controls are a no-template control, a no-primer control, calibration controls, and the first and second controls discussed above. Controls can be done in triplicate. To each tube, one adds 235 µl of binding buffer.

One also prepares a tube to measure the input by adding to an empty Eppendorf tube: 290 µl of binding buffer, which is equivalent to the volume in the tubes with matrix (235 µl of binding buffer, 15 µl of water, and 40 µl contributed by matrix volume). The input amount determination can be done in triplicate.

To the tubes containing matrix (the test samples and first and second controls), one adds 20 µl of sample. To the tubes containing buffer (the third control), one adds 20 µl of mock PCR amplification mixture. The tubes are then shaken on a Vortex Genie 2 mixer at a setting of 4 at room temperature for 30 minutes. The tubes are then centrifuged in an Eppendorf microfuge (16,000×g) for 5 minutes at room temperature. The upper 200 µl of supernatant from each tube is removed without disturbing the pellet or matrix present on the wall of the tube and placed in a clean Eppendorf tube.

The fluorescence of the supernatant is measured on a Hitachi Model 2000 in the cuvettes indicated above. For probes labeled with 7-diethylamino-3 (4'-maleimidophenyl)-4-methyl-coumarin, the spectrofluorometer is set as follows: PM voltage is 700 V; the excitation wavelength is 432 nm; the emission wavelength is 480 nm; the excitation slit width is 10 nm; and the emission slit width is 20 nm. One should minimize exposure of sample to excitation light; if the sample is to remain in the spectrofluorometer for a prolonged period, the shutter should be closed.

The number of pmoles of probe cleaved is the most convenient way of assessing the amount of signal. To assess the amount of signal, then, one first determines the input signal from the third control by the following calculation:

$$\frac{\left(\frac{\text{Fluorescence Signal of Third Control}-}{\text{Fluorescence Signal of First Control}}\right) \times (310/20)}{10 \text{ pmoles}}$$

In this formula, the subtraction corrects for any background fluorescence in the test sample; 310/20 is the dilution factor; and 10 pmoles is the amount of probe added to the PCR amplifications.

The amount of test sample signal is calculated by the following formula:

$$\frac{\left(\frac{\text{Fluorescence Signal of Test Sample}-}{\text{Fluorescence Signal of First Control}}\right) \times 310/20}{\text{Input Signal}}$$

The above protocol can be modified according to the particular fluorophore used to label the probe and is merely illustrative of the invention.

FIG. 16 shows typical results and relation of signal to input target number for the present method using Bakerbond™ PEI solid phase extractant.

We claim:

1. A kit for detecting a nucleic acid sequence in a sample comprising:
   (a) a set of oligonucleotide primers, wherein a first primer contains a sequence complementary to a region in one strand of the nucleic acid sequence and primes the synthesis of a first extension product, and a second primer contains a sequence complementary to a region in said first extension product and primes the synthesis of a nucleic acid strand complementary to said first extension product, and wherein each oligonucleotide primer is selected to anneal to its complementary template upstream of any labeled oligonucleotide annealed to the same nucleic acid strand,
   (b) at least one labeled oligonucleotide containing a sequence complementary to a region of the nucleic acid sequence, wherein said labeled oligonucleotide anneals within the nucleic acid sequence bounded by the oligonucleotide primers of part (a) and wherein said labeled oligonucleotide is blocked at the 3' terminus to prohibit incorporation of said labeled oligonucleotide into a primer extension product, wherein said blocking is achieved by adding a chemical moiety to the 3' hydroxyl of the last nucleotide, which moiety does not also serve as a label for subsequent detection or by removing said 3'-hydroxyl, and wherein said labeled oligonucleotide is provided in a soluble form and it generates a signal concurrently with the amplification of said nucleic acid sequence using said set of oligonucleotide primers.

2. The kit of claim 1, wherein said labeled oligonucleotide is not coupled to a membrane.

3. The kit of claim 1, wherein said labeled oligonucleotide is not coupled to a solid support.

4. The kit of claim 1, wherein said labeled oligonucleotide is not a gapped circle probe.

5. The kit of claim 1, wherein said labeled oligonucleotide anneals within the nucleic acid sequence concurrently with each oligonucleotide primer priming the synthesis of the first extension product or the nucleic acid strand complementary to the first extension product.

6. The kit of claim 1 further comprising an instruction, wherein the instruction provides a method for amplifying the nucleic acid sequence, generating a signal concurrently with the amplification of the nucleic acid sequence, and detecting said signal corresponding specifically to the presence of the nucleic acid sequence, thereby detecting the nucleic acid sequence.

7. The kit of claim 1, wherein said labeled oligonucleotide is blocked at the 3' terminus by adding a chemical moiety to the 3' hydroxyl of the last nucleotide of said labeled oligonucleotide, which chemical moiety is a phosphate group.

8. The kit of claim 1, wherein said labeled oligonucleotide is blocked at the 3' terminus by removing the 3'-hydroxyl from said labeled oligonucleotide.

9. The kit of claim 1 further comprising a nucleic acid polymerase having a 5' to 3' nuclease activity.

10. The kit of claim 9 wherein said nucleic acid polymerase is a thermostable enzyme.

11. The kit of claim 10 wherein said thermostable nucleic acid polymerase is a DNA polymerase from a *Thermus* species.

12. The kit of claim 1, wherein said labeled oligonucleotide contains at least two labels.

13. The kit of claim 1, wherein said labeled oligonucleotide contains a label at its 5' end or 3' end.

14. The kit of claim 1, wherein said labeled oligonucleotide contains a first label and a second label and wherein the first label and the second label interact with each other.

15. The kit of claim 1, wherein said labeled oligonucleotide contains a first label and a second label and wherein the first label and the second label are separated from each other by a nuclease susceptible cleavage site.

16. The kit of claim 15, wherein the first label is a fluorophore and the second label is a quencher.

17. The kit of claim 1, wherein said first labeled oligonucleotide contains a first label at its 5' end and a second label within said labeled oligonucleotide.

18. The kit of claim 1 further comprising a second labeled oligonucleotide.

19. The kit of claim 18, wherein the first labeled oligonucleotide contains a first label and the second labeled oligonucleotide contains a second label.

20. The kit of claim 18, wherein the first labeled oligonucleotide is complementary to a first region of the nucleic acid sequence and the second labeled oligonucleotide is complementary to a second region of the nucleic acid sequence, wherein the first labeled oligonucleotide is downstream of the first primer and the second labeled oligonucleotide is downstream of the second primer.

21. The kit of claim 18, wherein the presence of the first labeled oligonucleotide and the second labeled oligonucleotide increases the signal generated by the first labeled oligonucleotide.

* * * * *